(12) United States Patent
Salmon et al.

(10) Patent No.: US 12,364,492 B2
(45) Date of Patent: *Jul. 22, 2025

(54) THROMBECTOMY SYSTEM AND METHOD OF USE

(71) Applicant: Anaconda Biomed, S.L., Sant Quirze del Vallès (ES)

(72) Inventors: François Salmon, Le Celle Saint Cloud (FR); Ofir Arad Hadar, Sant Cugat (ES)

(73) Assignee: ANACONDA BIOMED, S.L., Sant Quirze del Vallès (ES)

(*) Notice: Subject to any disclaimer, the term of this patent is extended or adjusted under 35 U.S.C. 154(b) by 0 days.

This patent is subject to a terminal disclaimer.

(21) Appl. No.: 18/447,854

(22) Filed: Aug. 10, 2023

(65) Prior Publication Data

US 2024/0148395 A1 May 9, 2024

Related U.S. Application Data

(63) Continuation of application No. 17/500,844, filed on Oct. 13, 2021, now Pat. No. 11,771,446.
(Continued)

(51) Int. Cl.
*A61B 17/22* (2006.01)
*A61B 17/00* (2006.01)

(52) U.S. Cl.
CPC .... *A61B 17/22* (2013.01); *A61B 2017/00292* (2013.01); *A61B 2017/22072* (2013.01); *A61B 2017/22079* (2013.01)

(58) Field of Classification Search
CPC ........... A61B 17/22; A61B 17/221; A61B 2017/22079; A61B 2017/00292; A61B 2017/22072
See application file for complete search history.

(56) References Cited

U.S. PATENT DOCUMENTS

| 4,574,176 A | 3/1986 | Sharp |
| 4,794,231 A | 12/1988 | Banas et al. |

(Continued)

FOREIGN PATENT DOCUMENTS

| AU | 2018274903 B2 | 4/2020 |
| CN | 102973332 A | 3/2013 |

(Continued)

OTHER PUBLICATIONS

Medtronic; Medtronic.com; The Solitaire Platinum Revascularization Device; Model Specifications; DC00079632 Rev A ; 1 page; retrived from the internet (https//www.medtronic.com) on Mar. 2018.

(Continued)

*Primary Examiner* — Tuan V Nguyen
(74) *Attorney, Agent, or Firm* — Shay Glenn LLP

(57) ABSTRACT

A method of extracting a thrombus from a thrombus site in a cerebral artery of a patient by advancing a first catheter into an internal carotid artery of the patient; advancing a funnel catheter within the first catheter; moving the funnel catheter and the first catheter with respect to each other to place the funnel outside of the first catheter; expanding the funnel into contact with an inner wall of the internal carotid artery at or proximal to a distal end of a carotid siphon, thereby reducing blood flow past the funnel; advancing a clot-mobilizer distally through the first catheter toward the thrombus and beyond the carotid siphon; engaging thrombus material from the thrombus with the clot-mobilizer; moving the clot-mobilizer and thrombus material proximally at least partially into the funnel; applying suction to aspirate thrombus material; and moving the funnel, the clot-mobilizer and the thrombus material proximally within the vasculature.

7 Claims, 19 Drawing Sheets

Related U.S. Application Data

(60) Provisional application No. 63/093,540, filed on Oct. 19, 2020.

(56) References Cited

U.S. PATENT DOCUMENTS

| | | |
|---|---|---|
| 4,921,478 A | 5/1990 | Solano et al. |
| 5,011,488 A | 4/1991 | Ginsburg |
| 5,092,839 A | 3/1992 | Kipperman |
| 5,102,415 A | 4/1992 | Guenther et al. |
| 5,190,561 A | 3/1993 | Graber |
| 5,605,530 A | 2/1997 | Fishell et al. |
| 5,769,871 A | 6/1998 | Mers Kelly et al. |
| 5,908,435 A | 6/1999 | Samuels |
| 5,971,938 A | 10/1999 | Hart et al. |
| 5,972,019 A | 10/1999 | Engelson et al. |
| 6,066,149 A | 5/2000 | Samson et al. |
| 6,159,230 A | 12/2000 | Samuels |
| 6,190,303 B1 | 2/2001 | Glenn et al. |
| 6,402,771 B1 | 6/2002 | Palmer et al. |
| 6,514,273 B1 | 2/2003 | Voss et al. |
| 6,663,650 B2 | 12/2003 | Sepetka et al. |
| 6,695,858 B1 | 2/2004 | Dubrul et al. |
| 6,730,104 B1 | 5/2004 | Sepetka et al. |
| 6,752,819 B1 | 6/2004 | Brady et al. |
| 7,004,954 B1 | 2/2006 | Voss et al. |
| 7,108,677 B2 | 9/2006 | Courtney et al. |
| 7,578,830 B2 | 8/2009 | Kusleika et al. |
| 7,686,825 B2 | 3/2010 | Hauser et al. |
| 7,993,302 B2 | 8/2011 | Hebert et al. |
| 8,088,140 B2 | 1/2012 | Ferrera et al. |
| 8,298,257 B2 | 10/2012 | Sepetka et al. |
| 8,679,142 B2 | 3/2014 | Slee et al. |
| 8,758,364 B2 | 6/2014 | Eckhouse et al. |
| 8,784,441 B2 | 7/2014 | Rosenbluth et al. |
| 8,858,497 B2 | 10/2014 | Di Palma et al. |
| 8,864,792 B2 | 10/2014 | Eckhouse et al. |
| 8,940,003 B2 | 1/2015 | Slee et al. |
| 8,984,003 B2 | 3/2015 | Ahmed et al. |
| 9,005,237 B2 | 4/2015 | Eckhouse et al. |
| 9,034,008 B2 | 5/2015 | Eckhouse et al. |
| 9,186,487 B2 | 11/2015 | Dubrul et al. |
| 9,463,035 B1 | 10/2016 | Greenhalgh et al. |
| 9,561,121 B2 | 2/2017 | Sudin et al. |
| 9,585,741 B2 | 3/2017 | Ma |
| 9,700,331 B2 | 7/2017 | Grandfield et al. |
| 9,844,381 B2 | 12/2017 | Eckhouse et al. |
| 9,861,783 B2 | 1/2018 | Garrison et al. |
| 10,285,720 B2 | 5/2019 | Gilvary et al. |
| 10,292,804 B2 | 5/2019 | Wang et al. |
| 10,426,644 B2 | 10/2019 | Shrivastava et al. |
| 10,434,605 B2 | 10/2019 | Feth et al. |
| 11,013,523 B2 | 5/2021 | Jacobi et al. |
| 11,534,191 B2 | 12/2022 | Ros Fabrega et al. |
| 11,771,446 B2 | 10/2023 | Salmon et al. |
| 2003/0023299 A1 | 1/2003 | Amplatz et al. |
| 2003/0212430 A1 | 11/2003 | Bose et al. |
| 2003/0212439 A1 | 11/2003 | Schuler et al. |
| 2004/0024416 A1 | 2/2004 | Yodfat et al. |
| 2004/0073243 A1 | 4/2004 | Sepetka et al. |
| 2004/0098099 A1 | 5/2004 | McCullagh et al. |
| 2004/0143317 A1 | 7/2004 | Stinson et al. |
| 2004/0167565 A1 | 8/2004 | Beulke et al. |
| 2004/0199201 A1 | 10/2004 | Kellett et al. |
| 2004/0243102 A1 | 12/2004 | Berg et al. |
| 2004/0260333 A1 | 12/2004 | Dubrul et al. |
| 2005/0209678 A1 | 9/2005 | Henkes et al. |
| 2006/0058838 A1 | 3/2006 | Bose et al. |
| 2006/0064073 A1 | 3/2006 | Schonholz et al. |
| 2006/0155305 A1 | 7/2006 | Freudenthal et al. |
| 2006/0293744 A1 | 12/2006 | Peckham et al. |
| 2007/0118165 A1 | 5/2007 | DeMello et al. |
| 2007/0188165 A1 | 8/2007 | Kitanaka et al. |
| 2007/0198028 A1 | 8/2007 | Miloslavski et al. |
| 2007/0203559 A1 | 8/2007 | Freudenthal et al. |
| 2007/0208367 A1 | 9/2007 | Fiorella et al. |
| 2007/0213765 A1 | 9/2007 | Adams et al. |
| 2007/0276332 A1 | 11/2007 | Bierman |
| 2007/0288038 A1 | 12/2007 | Bimbo |
| 2008/0228209 A1 | 9/2008 | DeMello et al. |
| 2008/0269774 A1 | 10/2008 | Garcia et al. |
| 2008/0269798 A1 | 10/2008 | Ramzipoor et al. |
| 2009/0163846 A1 | 6/2009 | Aklog et al. |
| 2009/0198269 A1 | 8/2009 | Hannes et al. |
| 2010/0004607 A1 | 1/2010 | Wilson et al. |
| 2010/0030256 A1 | 2/2010 | Dubrul et al. |
| 2010/0222864 A1 | 9/2010 | Rivelli et al. |
| 2011/0160763 A1 | 6/2011 | Ferrera et al. |
| 2011/0213297 A1 | 9/2011 | Aklog et al. |
| 2011/0213392 A1 | 9/2011 | Aklog et al. |
| 2012/0059309 A1 | 3/2012 | Di Palma et al. |
| 2012/0065660 A1 | 3/2012 | Ferrera et al. |
| 2012/0083868 A1 | 4/2012 | Shrivastava et al. |
| 2012/0114017 A1 | 5/2012 | Bang et al. |
| 2012/0116440 A1 | 5/2012 | Leynov et al. |
| 2012/0179181 A1 | 7/2012 | Straub et al. |
| 2013/0261638 A1 | 10/2013 | Diamant et al. |
| 2013/0325055 A1 | 12/2013 | Eckhouse et al. |
| 2013/0325056 A1 | 12/2013 | Eckhouse et al. |
| 2014/0052161 A1 | 2/2014 | Cully et al. |
| 2014/0074144 A1 | 3/2014 | Shrivastava et al. |
| 2014/0155908 A1 | 6/2014 | Rosenbluth et al. |
| 2014/0243885 A1 | 8/2014 | Eckhouse et al. |
| 2014/0277015 A1 | 9/2014 | Stinis |
| 2015/0112376 A1 | 4/2015 | Molaei et al. |
| 2015/0157346 A1* | 6/2015 | Ferrera ............ A61M 25/09025 606/200 |
| 2015/0164666 A1 | 6/2015 | Johnson et al. |
| 2015/0231360 A1 | 8/2015 | Watanabe et al. |
| 2015/0257775 A1* | 9/2015 | Gilvarry ............ A61B 17/221 606/127 |
| 2015/0359547 A1 | 12/2015 | Vale et al. |
| 2016/0081704 A1 | 3/2016 | Jeon et al. |
| 2016/0256255 A9 | 9/2016 | Ma |
| 2017/0007164 A1 | 3/2017 | Vale et al. |
| 2017/0065299 A1 | 3/2017 | Gillespie et al. |
| 2017/0105743 A1 | 4/2017 | Vale et al. |
| 2017/0119408 A1 | 5/2017 | Ma |
| 2017/0119409 A1 | 5/2017 | Ma |
| 2017/0215900 A1 | 8/2017 | Lowinger et al. |
| 2017/0215902 A1 | 8/2017 | Leynov et al. |
| 2017/0239444 A1 | 8/2017 | Parker |
| 2017/0333060 A1 | 11/2017 | Panian |
| 2018/0028209 A1 | 2/2018 | Sudin et al. |
| 2018/0064454 A1 | 3/2018 | Losordo et al. |
| 2018/0126132 A1 | 5/2018 | Heilman et al. |
| 2018/0132876 A1 | 5/2018 | Zaidat |
| 2018/0206862 A1 | 7/2018 | Long |
| 2018/0318062 A1 | 11/2018 | Sudin et al. |
| 2018/0353196 A1 | 12/2018 | Epstein et al. |
| 2018/0361114 A1 | 12/2018 | Chou et al. |
| 2019/0110805 A1 | 4/2019 | Ulm, III |
| 2019/0167284 A1 | 6/2019 | Friedman et al. |
| 2019/0167287 A1 | 6/2019 | Vale et al. |
| 2019/0216476 A1 | 7/2019 | Barry et al. |
| 2019/0239907 A1 | 8/2019 | Brady et al. |
| 2019/0269425 A1 | 9/2019 | Sudin et al. |
| 2019/0269491 A1 | 9/2019 | Jalgaonkar et al. |
| 2019/0274810 A1 | 9/2019 | Phouasalit et al. |
| 2019/0298396 A1 | 10/2019 | Gamba et al. |
| 2019/0307471 A1 | 10/2019 | Friedman et al. |
| 2019/0336727 A1 | 11/2019 | Yang et al. |
| 2020/0000613 A1 | 1/2020 | Shrivastava et al. |
| 2020/0008822 A1 | 1/2020 | Eckhouse et al. |
| 2020/0085444 A1 | 3/2020 | Vale et al. |
| 2020/0205838 A1 | 7/2020 | Walzman |
| 2020/0281612 A1 | 9/2020 | Kelly et al. |
| 2021/0000582 A1 | 1/2021 | Chomas et al. |
| 2021/0059695 A1 | 3/2021 | Haran et al. |
| 2021/0068852 A1 | 3/2021 | Spence |
| 2021/0077134 A1 | 3/2021 | Vale et al. |
| 2021/0236150 A1 | 8/2021 | Arad Hadar |
| 2021/0393280 A1 | 12/2021 | Cortinas Villazon et al. |
| 2022/0000500 A1 | 1/2022 | Arad Hadar et al. |
| 2022/0265962 A1 | 8/2022 | Rios Garriga et al. |

(56) References Cited

U.S. PATENT DOCUMENTS

| | | |
|---|---|---|
| 2022/0354517 A1 | 8/2022 | Behan |
| 2023/0127145 A1 | 4/2023 | Arad Hadar et al. |
| 2023/0270461 A1 | 8/2023 | Garcia Sabido et al. |
| 2023/0301807 A1 | 9/2023 | Garcia Sabido et al. |

FOREIGN PATENT DOCUMENTS

| | | |
|---|---|---|
| CN | 104159525 A | 11/2014 |
| CN | 107198554 B | 2/2020 |
| EP | 1427087 A1 | 6/2004 |
| EP | 2662109 A1 | 11/2013 |
| EP | 3266391 A1 | 1/2018 |
| ES | 2341978 T3 | 6/2010 |
| ES | 2381099 T3 | 5/2012 |
| GB | 2498349 A | 7/2013 |
| JP | 2005500138 A | 1/2005 |
| WO | WO99/45835 A2 | 9/1999 |
| WO | WO02/087677 A2 | 11/2002 |
| WO | WO03/075793 A1 | 9/2003 |
| WO | WO2004/002564 A1 | 1/2004 |
| WO | WO2005/027751 A1 | 3/2005 |
| WO | WO2008/124567 A1 | 10/2008 |
| WO | WO2008/157202 A1 | 12/2008 |
| WO | WO2009/014723 A1 | 1/2009 |
| WO | WO2009/105710 A1 | 8/2009 |
| WO | WO2011/068924 A1 | 6/2011 |
| WO | WO2011/082319 A1 | 7/2011 |
| WO | WO2012/106657 A2 | 8/2012 |
| WO | WO2012/156924 A1 | 11/2012 |
| WO | WO2012/158269 A1 | 11/2012 |
| WO | WO2013/008233 A1 | 1/2013 |
| WO | WO2013/152327 A1 | 10/2013 |
| WO | WO2014/008460 A2 | 1/2014 |
| WO | WO2014/127389 A2 | 8/2014 |
| WO | WO2014/204860 A1 | 12/2014 |
| WO | WO2015/006782 A1 | 1/2015 |
| WO | WO2015/189354 A1 | 12/2015 |
| WO | WO2016/113047 A1 | 7/2016 |
| WO | WO2017/072663 A1 | 5/2017 |
| WO | WO2017/074290 A1 | 5/2017 |
| WO | WO2017/075544 A1 | 5/2017 |
| WO | WO2018/080590 A1 | 5/2018 |
| WO | WO2018/160966 A1 | 9/2018 |
| WO | WO2019/055311 A1 | 3/2019 |
| WO | WO2019/064306 A1 | 4/2019 |
| WO | WO2019/178131 A1 | 9/2019 |
| WO | WO2020/021333 A2 | 1/2020 |
| WO | WO2020/079082 A1 | 4/2020 |
| WO | WO2020/099386 A1 | 5/2020 |
| WO | WO2021/016213 A1 | 1/2021 |

OTHER PUBLICATIONS

Villazón et al., U.S. Appl. No. 18/641,098 entitled "Device and a thrombectomy apparatus for extraction of thrombus from a blood vessel", filed Apr. 19, 2024.

Garcia Sabido et al.; U.S. Appl. No. 18/722,456 entitled "An intravascular device with an improved attachment of its elements and a method of manufacturing thereof," filed Jun. 20, 2024.

Garcia Sabido et al.; U.S. Appl. No. 18/722,470 entitled "An intravascular device with an Improved attachment of its elements and a method of manufacturing thereof," filed Jun. 20, 2024.

Arad et al.; U.S. Appl. No. 62/760,786 entitled "Thrombectomy system comprising an expandable tip aspiration catheter and clot-capture element," filed Nov. 13, 2018.

Berkhemer et al.; A randomized trial of intraarterial treatment for acute ischemic stroke; New England Journal of Medicine; 372; pp. 11-20; Jan. 1, 2015.

Bouthillier et al.; Segments of the internal carotid artery: a new classification; Neurosurgery; 38(3); pp. 425-433; Mar. 1, 1996.

Castano et al.; Unwanted detachment of the Solitaire device during mechanical thrombectomy in acute ischemic stroke; Journal of neurointerventional surgery; 8(12); pp. 1226-1230; Dec. 1, 2016.

Ceretrieve; 3 pages; retrieved from the internet (http://trendlines.com/portfolio/ceretrieve/) on Sep. 13, 2018.

Duffy et al.; Novel methodology to replicate clot analogs with diverse composition in acute ischemic stroke; Journal of neurointerventional surgery; 9(5); pp. 486-491; May 1, 2017.

Fennell et al.; What to do about fibrin rich "tough clots"? Comparing the Solitaire stent retriever with a novel geometric clot extractor in an in vitro stroke model; Journal of neurointerventional surgery; 10(9); pp. 907-910; Sep. 1, 2018.

Mokin et al.; Stent retriever thrombectomy with the Cover accessory device versus proximal protection with a balloon guide catheter: in vitro stroke model comparison; Journal of neurointerventional surgery; 8(4); pp. 413-417; Apr. 1, 2016.

Penumbra Inc.; Recalls 3D revascularization device due to wire material that may break or separate during use; FDA Recall; retrieved from the internet (http://web.archive.org/web/20200813123505/https:/www.fda.gov/medical-devices/medical-device-recalls/penumbra-inc-recalls-3d-revascularization-device-due-wire-material-may-break-or-separate-during-use).

Garcia Sabido et al.; U.S. Appl. No. 18/546,190 entitled "An expandable clot mobilizer device for extraction of an occlusion from a blood vessel," filed Aug. 11, 2023.

Garcia Sabido et al.; U.S. Appl. No. 18/546,206 entitled "A self expandable medical device for advancement through vasculature to an expansion site in a blood vessel," filed Aug. 11, 2023.

\* cited by examiner

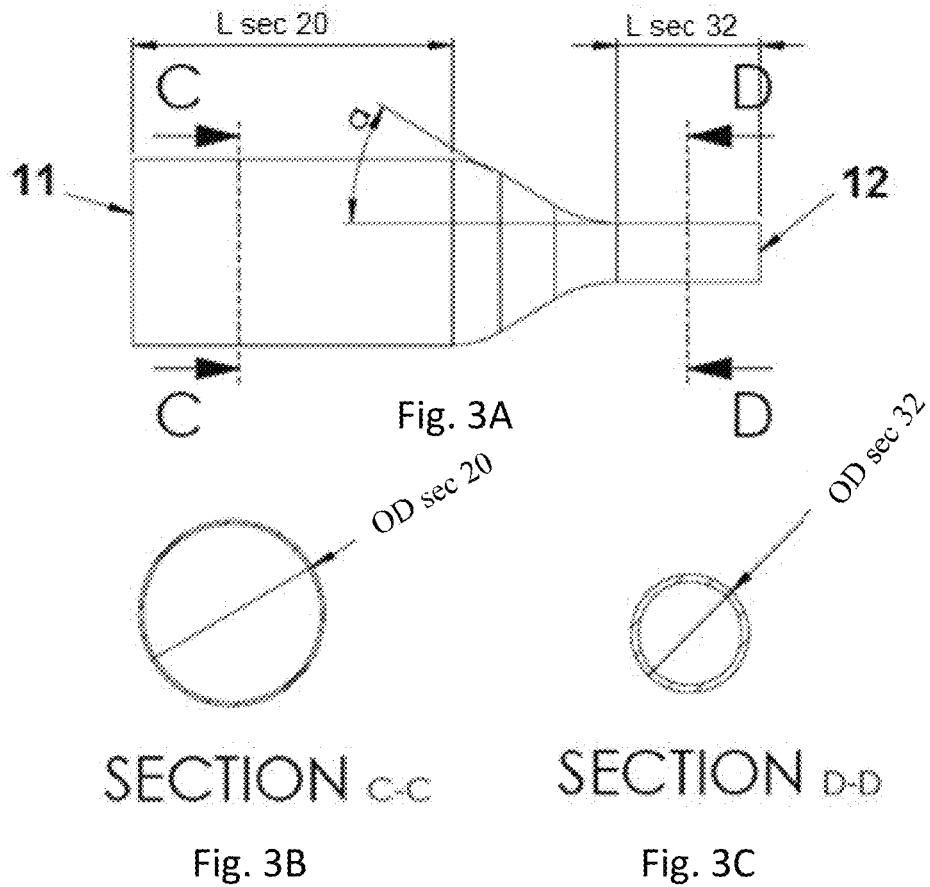
Fig. 3A
Fig. 3B
Fig. 3C
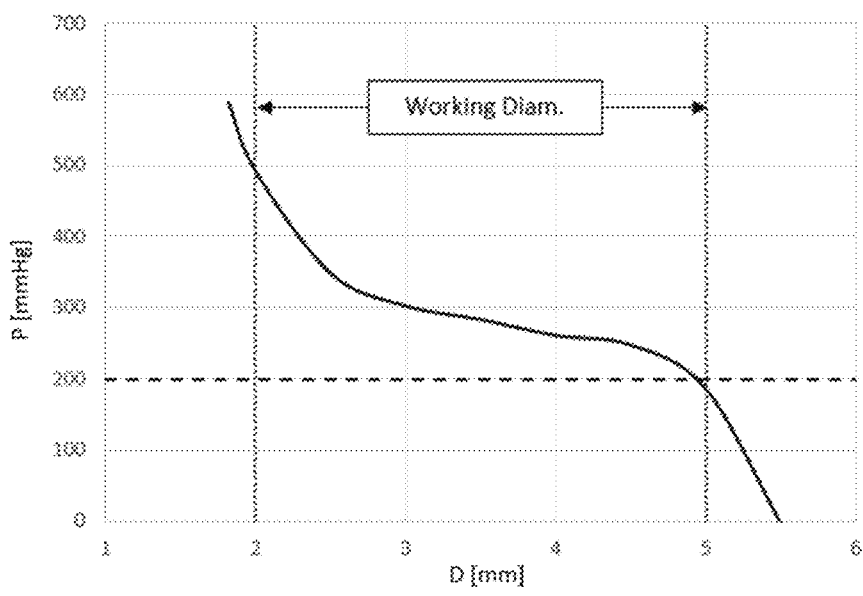
Fig. 4

Proximal and distal cross-sectional areas for each device

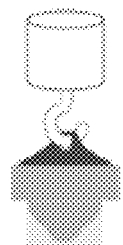
Fig. 30A　　　　Fig. 30B　　　　Fig. 30C
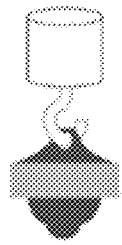
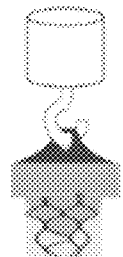
Fig. 30D　　　　Fig. 30E　　　　Fig. 30F

THROMBECTOMY SYSTEM AND METHOD OF USE

CROSS REFERENCE TO RELATED APPLICATIONS

This application is a continuation of U.S. patent application Ser. No. 17/500,844, filed Oct. 13, 2021, titled "THROMBECTOMY SYSTEM AND METHOD OF USE", which application claims the benefit of U.S. Provisional Patent Application No. 63/093,540, filed Oct. 19, 2020, titled "THROMBECTOMY SYSTEM AND METHOD OF USE", incorporated by reference herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates to use of a thrombectomy apparatus to remove thrombi at the vascular level. In some embodiments, the invention includes use of a combination of an expandable-tip catheter and a clot-mobilizer and the application of suction to remove vascular thrombi and thrombus material.

BACKGROUND

Acute ischemic stroke is a major cause of morbidity and mortality, with an annual incidence of 118 cases/100000 population and a mortality of 29 cases per 100000 population/year. These numbers position ischemic stroke as one of the main causes of death in developed countries together with cardiovascular diseases and cancer. In order to prevent or reduce complications related to this disease and to improve the prognosis of patients with ischemic stroke, it is necessary a clinical diagnosis to establish a proper reperfusion strategy in the shortest period of time. Until 2015 the treatment of choice for stroke was the recombinant tissue plasminogen activator (rtPA) administered intravenously 4.5 hours after symptom onset. However, this drug presents a narrow therapeutic window and not always gets recanalization. Consequently, intra-arterial recanalization therapy as mechanical thrombectomy is performed by means of various devices (Merci®, Penumbra®, etc.). The objective is to remove thrombus through aspiration, disruption or capture/extraction, viewed as a therapeutic option for patients who are not candidates for rtPA or in whom rtPA has failed. With the aim of improving the clinical outcomes achieved with these devices, stent retrievers appear to give this technique a more widespread use (Solitaire™, Trevo® and Revive).

Endovascular treatment of stroke has been performed since the 1990's. Its growth in the number of treated patients has been slow but constant. The main obstacle to its more widespread use is the necessity of a coordinated medical system at different levels to make it possible for patients to get to a medical center capable of administering these highly complex treatments within 6-8 hours of symptom onset.

Early strategies for the endovascular treatment of stroke provided local perfusion of a fibrinolytic agent through a catheter directly into the thrombus to dissolve blood clots. Beginning in the 2000 decade, a device that seemed to be more effective than intra-arterial fibrinolysis appeared. It was a spiral that unfolded around the thrombus, facilitating its extraction (the MERCK) retrieval system).

Starting in 2006, a new system became popular. A large-gauge catheter was designed to be advanced to the thrombus. The catheter was connected to a continuous aspiration pump to aspirate the thrombus (the Penumbra System®).

This system has evolved over the years, seeking to attain a catheter with an increasingly large diameter, able to navigate close to the thrombus.

In 2009, the use of stent retrievers started. Their use consists of crossing the thrombus with a microcatheter. Thereafter, the endoprosthesis is advanced through the microcatheter. Once the distal end of the microcatheter has reached the distal part of the thrombus, the endoprosthesis (stent retriever) is unsheathed, self-expanding through the thrombus and capturing it. It is recommended to wait a few minutes with the endoprosthesis expanded to enable proper engagement of the thrombus. The expanded stent is then withdrawn to drag the thrombus toward the catheter and out of the blood vessel. This last step can be done while aspirating through the catheter to try to reverse the blood flow in the vessel and to increase the likelihood of recovering the thrombus. In addition, when using a stent retriever, a guide balloon catheter is often used to slow or stop flow in the internal carotid artery while the stent retriever and aspiration catheter are advanced further distally to the site of the thrombus. The thrombus may be pulled distally from the occlusion site, and if the thrombus is not too large, into the balloon catheter by the stent retriever.

Stent retrievers have entirely displaced the first-generation devices described above due to their high efficacy and speed. Several prospective randomized trials have recently demonstrated the marked superiority of stent retriever assisted mechanical thrombectomy with standard intravenous tissue plasminogen activator (IV tPA) thrombolysis over medical therapy (IV tPA) alone for revascularization of acute ischemic stroke in patients presenting with proximal large vessel occlusion.

However, the use of stent retrievers presents different as-yet unsolved challenges:

Thrombus fragmentation. Stent retrievers may induce clot fragmentation causing distal embolization in a new territory (previously non-occluded vessels). Prior aspiration catheters used with stent retrievers have bores that are often smaller than the diameter of the clot, thereby exacerbating the clot fragmentation problem.

Once the clot has been moved from the occlusion site, if blood flow has not been stopped or significantly slowed (e.g., by a balloon catheter), flowing blood flow may fragment or dislodge the clot from the stent retriever and may cause a new occlusion, called a secondary embolism.

Prolonged revascularization time, as the fragmentation or detachment of the clot requires a multiple pass recanalization.

Navigability issues in small/tortuous vessels.

Furthermore, despite advances in revascularization tools for large vessel occlusion presenting as acute ischemic stroke, a significant subset of clots remains recalcitrant to current strategies. Occlusions involving fibrin rich thrombi are more difficult to recanalize, often requiring a greater number of passes with the device than thrombi with higher red blood cell content. Calcified thrombi are harder and more difficult to remove than softer cardiogenic thrombi using either a stent retriever or an aspiration approach. A calcified clot resists the stent retracting movement. Calcified thrombi are also difficult to remove by aspiration methods, since they have a harder consistency and tend to be densely packed within the vessel making it difficult to place the catheter tip within the calcified clot to maintain the vacuum needed for aspiration.

SUMMARY OF THE DISCLOSURE

The present invention provides thrombectomy systems and methods to improve the efficacy of removing vascular thrombi, particularly in the cerebral vasculature. The system employs an aspiration catheter and a clot-mobilizer (i.e., a device that can engage and move a thrombus or thrombus material in a blood vessel, e.g., toward the aspiration catheter), such as a stent retriever. The systems and methods of this invention may be used in clinical situations (e.g., tortuosity at the carotid siphon) presenting difficult navigation to the occlusion site by providing more effective aspiration at a location proximal to the tortuosity and distant from the occlusion site. The system and method are particularly effective in capturing hard clots such as fibrin rich clots in the cerebral vasculature.

Methods of the present invention may be practiced by using a thrombectomy system such as that described in WO2016113047A1, WO2020099386A1 and WO2020079082A1, all of which are herein incorporated by reference in their entirety. The thrombectomy system comprises a self-expanding funnel that expands to engage the vessel wall so that it locally restricts or stops blood flow. Suction can be applied to a funnel catheter extending proximally from the funnel so that the funnel aspirates clots and clot fragments to reduce secondary embolism. When used in combination with a clot-mobilizer, such as a stent retriever, some or all of the entire clot can be mobilized into the funnel. In addition, the funnel is designed to adapt its shape to the vasculature so that it lengthens as it narrows during withdrawal to retain the captured clot material within the funnel.

One potential obstacle of any intravascular cerebral artery intervention is the tortuosity of the arterial vasculature, particularly in parts of the internal carotid artery. The carotid siphon is a bending and curving portion of the internal carotid artery (including segments C4 (cavernous), C5 (clinoidal) and C6 (ophthalmic) according to the Bouthillier classification (described in Bouthillier A, et al., Segments of the internal carotid artery: a new classification, Neurosurgery 1996, vol. 38, pp. 425-32), as it enters the dura mater forming the roof of the sinus. The apex of the carotid siphon is the central part of the curve (generally at segment C5 of the Bouthillier classification). The distal end of the carotid siphon is the distal end of segment C6 of the Bouthillier classification. While WO2020099386A1 describes advancing the delivery catheter and the funnel to a position just proximal to the thrombus, in some situations it might not be desirable, or even possible, to navigate the delivery catheter and funnel through the carotid siphon. The present invention provides a thrombectomy system that provides clinicians the ability to perform different clinical methods, as needed, including (1) deployment of a funnel at or near a thrombus site in the cerebral vasculature (i.e., by navigating the delivery catheter and funnel through the carotid siphon) to reduce or stop blood flow and aspirate thrombus material at or near that site; (2) deployment of the funnel in or proximal to the carotid siphon to reduce or stop blood flow and aspirate thrombus material at a site in or proximal to the carotid siphon while advancing the smaller diameter clot-mobilizer microcatheter through the carotid siphon to the thrombus site beyond the carotid siphon in a cerebral vessel, thereby reducing overall procedure time; and (3) deployment of the funnel in or proximal to the carotid siphon to reduce or stop blood flow at a site in or proximal to the carotid siphon while advancing a separate distal access catheter (instead of, or in addition to, a clot-mobilizer and its microcatheter) through the funnel to the thrombus site beyond the carotid siphon in a cerebral vessel to aspirate thrombus material. Surprisingly, the second method listed above of using the thrombectomy system provides a clinical efficacy as good as, or better than, the first method, as described below. In all scenarios, the system of this invention effectively restricts blood flow past the funnel during retrieval of the clot and aspirates the clot for safe removal from the patient.

In an embodiment, the delivery catheter, the funnel and funnel catheter, the microcatheter and the clot-mobilizer are oriented on the same axis, are coaxially configured and movable to each other independently.

In an embodiment, the funnel is self-expandable.

The thrombectomy system of the invention can be used in the neurovasculature or in the peripheral vasculature. The funnel is particularly suited to navigate to the desired location i.e., at or near the thrombus or at a more proximal location. The funnel is a self-expandable structure covered with a non-permeable cover that provides an outward radial force against the wall of the blood vessel in which it expands to provide an effective restriction of blood flow past the funnel, thus avoiding development of secondary thrombi. Its design allows the introduction of a retrieval device through it that actuates as a clot-mobilizer to move a thrombus, or thrombus material, into the funnel mouth. The funnel is operated with the use of a funnel catheter that enables navigation and positioning of the funnel. Moreover, the funnel catheter may be used to provide suction from its proximal end, where the vacuum is generated by an interventionist (e.g., with a syringe), to the vicinity of the funnel at the distal end of the catheter.

This coated funnel can be in retracted or extended configurations, the diameter of the funnel being bigger in the extended configuration than in the retracted configuration. Additionally, the funnel is designed not to cause damage to the blood vessel in which it is expanded. The coated funnel expands with an outward radial force to the diameter of the artery and, as a result, stops or restricts the blood flow in that artery, which is one of the most important characteristics of the described system for the prevention of distal embolism. Distal embolism is a typical clinical complication when a stent retriever crosses a clot or during the extraction process.

The expansion behavior of the funnel is due to the Nitinol material from which it is formed, thanks to its shape memory properties and super elasticity. Shape memory refers to the ability to undergo deformation and then recover its original shape by heating the material above its transformation temperature. In combination with super elasticity, Nitinol presents the right characteristics to position to different diameters and geometries of the vessel.

An in vitro study with 3D cerebrovascular models was performed to compare the rate of vascularization of the thrombectomy system of the present invention compared to the standard use of a stent retriever with a balloon guide catheter (BGC) and the Solumbra approach (Distal Access Catheter, DAC+ stent retriever). The results of the study are shown below in the Examples section. Remarkably, the thrombectomy system of the invention is superior in terms of in vitro revascularization to BGC or Solumbra. This is especially relevant with fibrin rich clots. In other words, the thrombectomy system of the invention performs better compared to different combinations of aspiration with a stent retriever.

Further, advantages of the thrombectomy system can be summarized as follows: The funnel, a self-expandable structure (formed, e.g., from Nitinol) sealed with a film of non-permeable polymeric material, upon deployment expands to the blood vessel dimensions. Advantageously, the large mouth of the funnel together with the clot-mobilizer moves and aspirates thrombus material or the entire thrombus without further fragmenting it and also allocates the clot perfectly during the removal procedure. The loss of the clot due to the long distance from the occlusion site to the exit and also due to the large size of the clot (making it difficult for the clot-mobilizer to retain on its own) is also prevented, due in part to the ability of the funnel to lengthen as it narrows as it moves through the vasculature. The system is able to restrict blood flow in the vessel and, as a result, increases the aspiration power of the system and reduces further clinical side complications, mainly distal embolism. The system also provides clinicians the choice of navigating the funnel up to the clot so that blood flow is restricted or stopped directly at the thrombus site so that only a particular arterial branch is affected, or deploying the funnel at some distance proximal to the clot, thereby avoiding the extra procedure time required to navigate the delivery catheter and the funnel through tortuous vasculature. Surprisingly, as discussed with respect to the examples below, because of the unique design of the thrombectomy system general and the funnel in particular, deployment of the funnel in or proximal to the carotid siphon does not detract from the overall efficacy of the system in safely removing clots from the distal cerebral vasculature.

Clot-Mobilizer

A clot-mobilizer in the present description is a device able to interact with a clot in order to move the clot, or thrombus material, in the blood vessel. This definition includes the following categories without being limiting for the present invention:

Coil retriever system. This category includes first generation of clot-capture elements like the Merci® retriever system, which is a helically-tapered cork screw like catheter tip. The second generation incorporates a helical coil at 90° with respect to the proximal catheter along with added filaments. And the third generation is a hybrid design of non-tapered, non-angulated filamented helical coil to allow for maximal clot retention.

Stent retriever, which is in this description a device normally with a metallic mesh which operates through a metallic pusher, able to capture the clot by retrieving it within its struts. Examples of stent retrievers include the following:

Solitaire FR (Medtronic Neurovascular)

Trevo™ XP ProVue Retrieval System (Stryker)

Embotrap (Neuravi)

Revive PV (DePuy Synthes)

pReset (Phenox)

Eric (Microvention)

MindFrame Capture LP System (Covidien)

APERIO (Acandis GmbH)

Catch (B alt Extrusion)

Tigertriever (Rapid Medical)

Stream (Perflow Medical)

Jrecan

3D Revascularization device (Penumbra)

Neva (Vesalio)

Versi (Neurovasc Technologies)

Other types of clot-mobilizers include:

Golden Retriever (Amnis)

Triticum Medical

ClotTriever thrombectomy device (Mari Medical)

Dais-e (Mivi Neuroscience)

Navimax (Intratech Medical)

ThromboWire (Capture Vascular Systems)

In an embodiment, the clot-mobilizer is a stent retriever device. More particularly the stent retriever device has closed cells like Solitaire or Trevo.

Expandable-Tip Catheter Comprising a Funnel

In an embodiment, the funnel comprises a segment defining a distal end and a proximal end and is configured to adapt at least its shape to a surrounding blood vessel from a retracted position in a compressed state (also referred as "in a delivery configuration"), particularly inside a carrier, for example a delivery catheter or a guide catheter (or sheath), to an extended and expanded position (also referred as "in a deployment configuration"), to be appositioned against the inner wall of a blood vessel to receive and retain a thrombus or thrombus material.

Unlike other expandable-tip catheters, the funnel of this invention, which is self-expandable, is formed by a mesh of at least two sets, equal or different, of helicoidal filaments (or wires) turning respectively in opposite directions and being intertwined. Likewise, the mesh comprises a first tubular section, particularly of a uniform diameter, and a second tubular section, adjacent to the first section, having a diameter smaller than that of the first tubular section. The mesh of the funnel is covered by a non-permeable covering.

The mesh of the first section has a variable density of the helicoidal filaments to provide radial forces, i.e., pressure, higher than in the second section, such that the first section becomes better appositioned, or overlapped, against the inner wall of the blood vessel.

In an embodiment, the radial forces in first and second end portions (or extremes) of the first section are higher than in an intermediate portion of this first section. Alternatively, the radial forces in the first section can be uniformly distributed. Moreover, in the funnel of this invention, the filaments of each set are configured to abruptly turn and adopt an opposite direction at the first end portion of the first section, such that the filaments define at the distal end a closed loop crown. For example, by the first portion of the first section, i.e. the portion closer to said distal end, having closed loops the expansion of the funnel (once it comes out of the carrier) is facilitated. Thus, the radially outward forces of the funnel are increased. The cited loops also provide a smooth end to the funnel thus reducing the possible vessel damage and improving navigability conditions of the funnel within the blood vessel. Other options for increasing the radial forces are by having a single thread mesh in the first section, or by the first section having some weld spot, or by the density, composition or diameter of the mesh being higher.

The straight shape of the first section of the funnel creates a space which will accommodate the thrombus once it has been aspirated. The first section is adaptable to the vessel geometry and its outer surface overlaps the inner wall of the blood vessel.

Particularly the second section comprises two sub-sections, a first sub-section having a progressive reduction of diameter, with a shape configured to open and create a space for the thrombus, such as a cone-shape or a funnel-shape, and to stop a proximal blood flow during the removal of the thrombus, and a second sub-section of a tubular uniform diameter configured to provide a connection to a catheter or to a hypotube (with appropriate connectors at the proximal end).

The funnel can be produced in different sizes. In an embodiment, the first section is longer than the second section. In an embodiment, the first section comprises a length ranging between 4 and 40 millimeters and an outer diameter ranging between 3.5 and 7 millimeters, for example 5.2 mm, and the second sub-section comprises a length ranging between 1 and 10 millimeters and an outer diameter ranging between 1 and 2 millimeters, for example between 1.66 and 2 mm. Moreover, the shape of the first sub-section has a generatrix with an angle (a) comprised between 15 and 45 degrees with regard to a longitudinal axis of the funnel. This angle favors having more radial force thereby stopping the flow, but at the same time that there is a seal of the blood vessel it also has to allow the funnel to be compressed.

In another embodiment, the funnel further comprises a coating (or covering), hydrophilic or hydrophobic. The coating can be disposed over the first section only or over the first and second sections. In this latter case, a portion of the second section besides the proximal end is preserved uncoated. In another embodiment, the funnel comprises a coating, hydrophilic or hydrophobic, disposed over the second section only, particularly over the first sub-section of the second section. Besides, the funnel coating comprises a polymer such as a silicone or polyurethane.

Moreover, the coating may comprise holes, thus avoiding collapse of the funnel due to upstream blood pressure. Another option to avoid the collapse of the funnel is by the threads of the mesh having different diameter, thereby strengthening the funnel.

The helicoidal filaments of the mesh can be made of a metal, a metal alloy or a composite including Nitinol or Nitinol/Platinum, among others. The helicoidal filaments of the mesh can be made of Niti #1-DFT® (Drawn Filled Tubing), with a percentage of Platinum from 10% to 40%; in particular with 20% Platinum (Niti #1-DFT®-20% Pt) or 40% Platinum (Niti #1-DFT®-40% Pt).

The helicoidal filaments, in an embodiment comprise a number ranging between 24 and 48 filaments. In this case, the filaments have a cross section comprised in a range between 40 and 60 μm and the angle of the filaments with regard to the longitudinal axis of the funnel is comprised between 50 and 65 degrees for the first section, and between 15 and 50 for the second sub-section.

The funnel may also include or have attached thereto one or more sensors to provide information thereof. For example, a lighting sensor or sensors may provide information of whether the funnel is in the retracted position within the carrier or in the extended and expanded position. The sensor(s) can alternatively, or additionally, provide information on whether the funnel is well extended and expanded, on whether the thrombus is in or out, about the composition of the thrombus, or about the position of the funnel in relation to the blood vessel. Alternatively, the sensor(s) may include a piezoelectric sensor providing information about the radial forces in each of the different sections or subsections of the funnel.

Advantageously, the funnel of this invention can also comprise at least one radiopaque marker at its distal end and/or other strategic point(s) of the mesh which allow a physician to know the precise location of the funnel while using fluoroscopy.

In an embodiment, the funnel is disposed on a distal end of an aspiration catheter or expandable-tip catheter or funnel catheter. For example, the proximal end of the second sub-section of the funnel is connected to the distal end of the funnel catheter.

Guide Catheter

In an embodiment, the thrombectomy system of the present invention further comprises a guide catheter or sheath. A guide catheter allows the access of other devices through the vasculature, proximal to the thrombus site. One example is Neuronmax 088 (from Penumbra). A guide catheter can have an outer diameter ranging between 7 and 9 French and an inner diameter ranging between 5 and 6 French. The guide catheter can be used in radial access or femoral access, among others. In some embodiments, the guide catheter is guided by a guide wire (e.g., with a diameter of 0.035 in). In some embodiments, the guide catheter can be used in conjunction with other devices such as a diagnostic catheter (to deliver diagnostic agents) which transmits stiffness to the guide catheter in order to reach target sites. In other embodiments, the guide catheter, additional devices (e.g., diagnostic catheter) and the guide wire can also comprise a bending/oriented tip to improve the advancement of the catheter toward the target site.

Delivery Catheter

Embodiments of the thrombectomy system and method employ a delivery catheter to advance the funnel catheter and funnel beyond the distal end of a guide catheter or sheath. The delivery catheter has a smaller diameter than the guide catheter so that its distal end can navigate smaller and more tortuous vasculature on its way to the desired funnel deployment site. Use of a delivery catheter is optional. When the desired funnel deployment site is a location that can be reached by a guide catheter, the funnel catheter and funnel can be advanced within the guide catheter without using a delivery catheter, and the funnel can be deployed through relative movement of the guide catheter and funnel at the funnel deployment site.

Distal Access Catheter

In an embodiment, the thrombectomy system of the present invention further comprises a distal access catheter such as Navien (from Covidien) or Sofia (from MicroVention-Terumo) in order to reach the target site and withdrawn the thrombus or thrombus material by applying aspiration through a distal access catheter lumen. Distal access catheters are commonly used in mechanical thrombectomy. A distal access catheter can have an outer diameter ranging between 4 and 6 French, for example 5 French. The distal access catheter can be advanced through the funnel catheter (or expandable-tip catheter) and the guide catheter (or sheath). In an embodiment of the present invention, the delivery catheter, the funnel catheter, the guide catheter, the distal access catheter, the microcatheter and the clot-mobilizer are oriented on the same axis, are coaxially configured and movable to each other independently.

A Method of Extracting a Thrombus Using the Thrombectomy System of the Invention Another aspect of the invention relates to a method of extracting a thrombus from a thrombus site in a blood vessel of a patient using the thrombectomy system of the invention, the method comprising: advancing the delivery catheter and the funnel through vasculature of the patient toward the thrombus site with the funnel disposed in a retracted position proximal to the distal end of the delivery catheter; moving the funnel and delivery catheter with respect to each other to place the funnel in an extended position at least partially outside of the delivery catheter allowing the deployment of the funnel to its extended position, and thus, allowing to reduce or stop the blood flow in the blood vessel; advancing a microcatheter carrying a clot-mobilizer through a lumen of the funnel toward the thrombus site and into the thrombus; retracting the microcatheter to deploy the clot-mobilizer and move the thrombus or thrombus material toward the funnel; aspirating the thrombus or thrombus material with the funnel; and moving the funnel and the thrombus or thrombus material proximally within the vasculature.

Another aspect of the invention relates to a method of extracting a thrombus from a thrombus site in a cerebral artery of a patient, the method comprising: advancing a first catheter through vasculature of the patient into an internal carotid artery of the patient; advancing a funnel catheter within the first catheter, a funnel being disposed on a distal end of the funnel catheter; moving the funnel catheter and the first catheter with respect to each other to place the funnel outside of the first catheter; expanding the funnel into contact with an inner wall of the internal carotid artery at or proximal to a distal end of a carotid siphon (e.g., between the apex and the distal end of the carotid siphon, proximal to the apex of the carotid siphon, or proximal to the proximal end of the carotid siphon), thereby reducing or stopping blood flow past the funnel; advancing a clot-mobilizer distally through the first catheter toward the thrombus and beyond the carotid siphon; deploying the clot-mobilizer; engaging thrombus material from the thrombus with the clot-mobilizer; moving the clot-mobilizer and thrombus material proximally at least partially into the funnel; applying suction through the funnel catheter to the funnel to aspirate thrombus material; and moving the funnel, the clot-mobilizer and the thrombus material proximally within the vasculature.

In some or all embodiments of this aspect of the invention, the step of applying suction through the funnel catheter begins when the clot-mobilizer is disposed adjacent to a distal end of the funnel. Alternatively, in some or all embodiments of this aspect of the invention, the step of applying suction through the funnel catheter begins when the clot-mobilizer moves proximally at least part way into the funnel.

In some or all embodiments of this aspect of the invention, the clot-mobilizer is expanded into contact with an arterial wall. In some such embodiments, the clot-mobilizer is deployed after expanding the funnel, and in other embodiments the clot-mobilizer is deployed before expanding the funnel.

In some or all embodiments of this aspect of the invention, the first catheter is a delivery catheter, and the method further includes the steps of advancing a guide catheter through the internal vasculature and advancing the delivery catheter through the guide catheter. In other embodiments, the first catheter is a guide catheter. Alternatively, in some of all embodiments, the first catheter is advanced to the internal carotid artery without using a guide catheter.

In any or all such embodiments, the funnel adapts its shape and length to the vasculature as it moves proximally within the vasculature by lengthening as it narrows to retain the thrombus material at least partially within the funnel.

Instead of, or in addition to, using a clot-mobilizer device, a distal access catheter can be used to aspirate and extract the thrombus or thrombus material from the blood vessel. Thus, another aspect of the invention relates to a method of extracting thrombus material from a thrombus site in a cerebral artery of a patient, the method comprising: advancing a first catheter through vasculature of the patient into a carotid artery (e.g., an internal carotid artery) of the patient; advancing a funnel catheter within the first catheter, a funnel being disposed on a distal end of the funnel catheter; moving the funnel catheter and the first catheter with respect to each other to place the funnel outside of the first catheter; expanding the funnel into contact with an inner wall of the carotid artery at or proximal to a distal end of a carotid siphon (e.g., between the apex and the distal end of the carotid siphon, proximal to the apex of the carotid siphon or proximal to the proximal end of the carotid siphon), thereby reducing or stopping blood flow past the funnel; advancing a distal access catheter distally through the funnel catheter toward the thrombus and beyond the carotid siphon; applying suction through the distal access catheter to aspirate thrombus material from the thrombus; moving the distal access catheter and the thrombus material proximally at least partially into the funnel; and moving the funnel, the distal access catheter and the thrombus material proximally within the vasculature out of the body.

In some or all embodiments, the method according to this aspect of the invention also includes, prior to the step of applying suction, the steps of advancing a microcatheter carrying a clot-mobilizer through a lumen of the funnel toward the thrombus site and into the thrombus; retracting the microcatheter to deploy the clot-mobilizer; and engaging thrombus material from the thrombus with the clot-mobilizer.

In some or all of these embodiments, the first catheter is a delivery catheter, and the method includes the optional additional steps of advancing a guide catheter through the internal vasculature and advancing the delivery catheter through the guide catheter. Alternatively, the first catheter may be advanced to the internal carotid artery without using a guide catheter. In yet another embodiment, the first catheter is a guide catheter.

In some or all of these embodiments, the funnel may adapt its shape and length to the vasculature as it moves proximally within the vasculature by lengthening as it narrows to retain the thrombus material at least partially within the funnel.

BRIEF DESCRIPTION OF THE DRAWINGS

The previous and other advantages and features will be more fully understood from the following detailed description of embodiments, with reference to the attached figures, which must be considered in an illustrative and non-limiting manner, in which:

FIGS. 3A-C schematically illustrate some of the main specifications of the funnel.

FIG. 4 is a graph showing ideal pressure vs. diameter curve of the funnel.

FIGS. 30A-F show dynamometer models used to evaluate the suction force of various catheters. The dynamometer was connected to the catheter using a tool that simulates a hard clot. The experiment was performed without using a stent retriever (FIGS. 30A-C) and using a stent retriever (FIGS. 30D-F).

DETAILED DESCRIPTION

Figure 1:
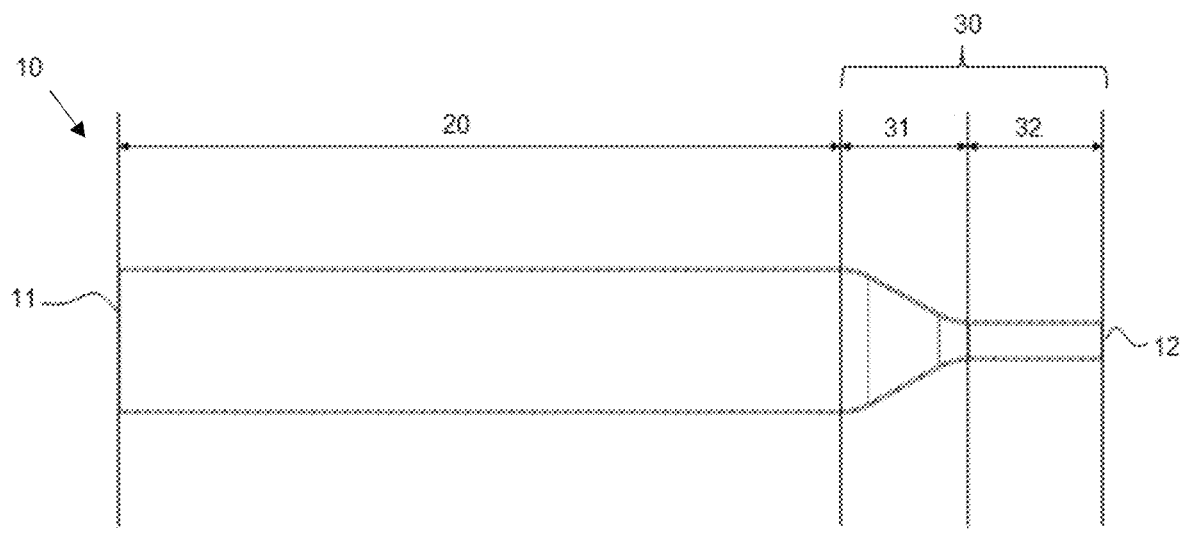
FIG. 1 schematically illustrates the different sections included in the funnel for extraction of thrombus or thrombus material from a blood vessel, according to an embodiment of the present invention.

FIGS. 1-3 and 5 show particular embodiments of a funnel 1 at the distal end of a funnel catheter 2 of a thrombectomy system (also called ANCD hereinafter) for extraction of thrombus material from a blood vessel. The funnel 1 includes a segment 10 which is self-expandable and defines a distal end 11 and a proximal end 12. The funnel 1 can exert an outward radial force in order to adapt its shape to a surrounding blood vessel from a retracted position in a compressed state, for example inside a carrier such a guide catheter (or sheath) or a delivery catheter 3, to an extended and expanded position, once coming out of the delivery catheter 3, to be appositioned against the inner wall of a blood vessel to slow or stop blood flow and to receive and retain a thrombus THR. In some embodiments of the invention, a guide catheter or sheath (not shown) is inserted into the patient's vasculature (e.g., through a femoral artery access point) and advanced toward a thrombus site in the vasculature. A delivery catheter 3, with funnel 1 compressed to fit within the inner diameter of delivery catheter 3, is then advanced to the funnel deployment site. In other embodiments, as described below, the method omits the delivery catheter, and the funnel catheter 2 and funnel 1 are advanced to the funnel deployment site within the guide catheter or sheath. As described below, the funnel deployment site may be at or just proximal to the thrombus (the "thrombus site"), or the funnel deployment site may be at a point in the vasculature significantly proximal to the thrombus site.

Figure 2:
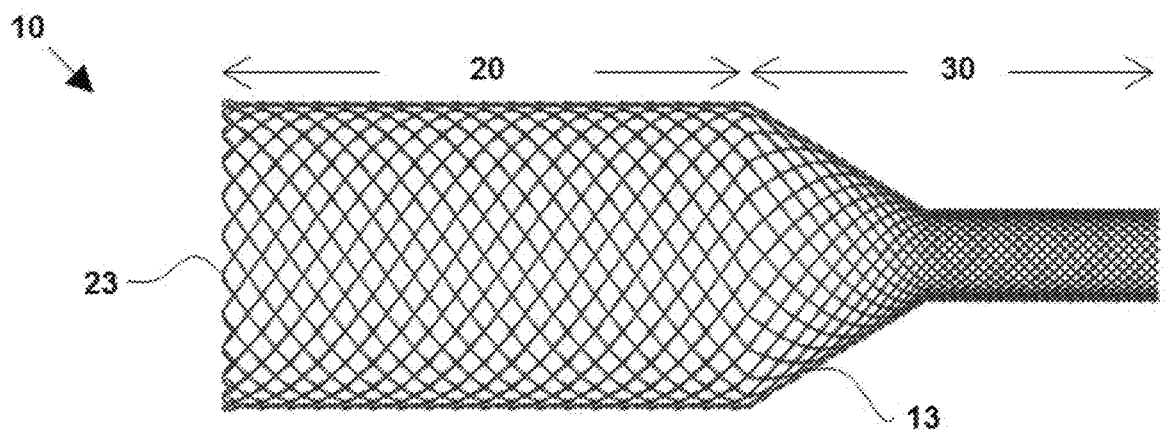
FIG. 2 illustrates the mesh included in the different tubular sections of the funnel having a lower mesh density in the first section than in the second section.

As shown in FIG. 2, the segment 10 comprises a mesh 13 having two sets of helicoidal filaments turning respectively in opposite directions and being intertwined. The mesh 13 in an embodiment can follow a diamond-type structure or a regular structure. The density of the mesh 13 defines the elasticity of the segment 10. As detailed in Table 1 the mesh angle (or braiding angle β) with regard to a longitudinal direction can be variable.

The helicoidal filaments can be made of a metal (including metal alloys), polymers, a composite including Nitinol or Nitinol/Platinum, or also DFT (Drawn Filled Tubing), among other materials having suitable mechanical properties.

As can be seen in FIGS. 1 and 2, the mesh 13 defines two distinct sections, a first section 20 and a second section 30. Particularly, the second section 30 comprises two sub-sections, a first sub-section 31 and a second sub-section 32.

As can be seen in FIG. 2, in this particular embodiment, the end portion of the first section 20 at the distal end 11 comprises closed loops 23 facilitating the expansion of the segment 10 once it comes out of the cited delivery catheter 3. Moreover, these closed loops 23 act as a spring or fixing point by limiting the movement between the helicoidal filaments and thus increasing the outward radial force. The closed loops 23 also provide a smooth distal end to reduce possible vessel damage and improve navigability of the funnel 1 within the blood vessel. The rest of the first section 20 creates the space which will accommodate the thrombus THR once it has been aspirated. The first section 20 is adaptable to the vessel geometry and, because of its configuration (e.g., diameter and braiding angle β), provides outward radial forces higher than in the second section 30 so that the segment 10 is better appositioned against the inner wall of the vessel. The radial forces in the end portions of the first section 20 are particularly higher than in an intermediate portion thereof, e.g., because of the spring action of closed loops 23. Alternatively, the radial forces in the first section 20 could be uniformly distributed along all its generatrix.

The first sub-section 31 (or portion of the second section 30 adjacent to the first section 20) is cone-shaped or funnel-shaped. Because of its shape, this sub-section 31 has features enabling it to withstand the blood pressure without collapsing. In the illustrated embodiment, the braiding angle α changes at the proximal and distal ends of sub section 31 provide radial strength to maintain the conical shape. The braiding angle α change at the distal end of sub-section 31 also works with the closed loops 23 to maintain first section 20 in an open position and create the space for the thrombus THR. The covering over sub-section 31 stops the blood flow during the capture and removal of the thrombus THR and protects the captured thrombus THR during the withdrawal of the segment 10 to the delivery catheter 3. This sub-section 31 is also the transition from the larger diameter of section 20 to the smaller diameter of sub-section 32 for connection to an aspiration catheter (or funnel catheter) 2 (see FIG. 5), or alternatively to a hypotube.

The second sub-section 32 (or portion of the second section 30 adjacent to proximal end 12) has a tubular uniform diameter and provides the connection to the funnel catheter 2. In some embodiments, the funnel catheter 2 is a PTFE-lined braided catheter covered by an outer jacket. The funnel catheter's braid and liner extend distally from the outer jacket. A layer of polymer material may be placed around the protruding braid and liner, and a mandrel may be placed within the braid and liner. Thereafter, the second sub-section 32 of segment 10 may be placed over this polymer section, and another layer of polymer may be placed over the mesh of subsection 32. This outer layer of polymer material is then melted so that polymer flows through the cells of the mesh 13, the mandrel is removed, and a smooth surface is left over the entire funnel catheter 2. This attachment approach adds structure and stiffness to the attachment section of the funnel catheter 2, so it should be as short as possible without compromising the integrity of the attachment of segment 10 to the funnel catheter 2.

Other techniques of connecting segment 10 to the funnel catheter 2 may be used, as understood by skilled artisans. For example, in other embodiments, if the funnel catheter 2 is a metal hypotube, the mesh 13 of the sub-section 32 is welded to a Nitinol ring. This ring is welded directly to the hypotube. Alternatively, a stainless-steel ring can be glued to the mesh 13 of the sub-section 32. Then, the stainless-steel ring is welded to the hypotube. Another option is to directly mesh the segment 10 over a perforated ring so that the filaments pass through the holes. When the segment 10 is compressed inside the delivery catheter 3, segment 10 elongates to move the helicoidal filaments toward a longitudinal alignment so as to reduce the spring effect and to facilitate the movement of segment 10 within the delivery catheter 3 by reducing friction effects and by increasing pushability. The pushability of the segment 10 inside the delivery catheter 3 is related to the navigability of the segment 10 within the arteries.

The mesh angle or braiding angle β allows the mesh 13 to be adapted to a curve of the blood vessel, avoiding the kinking and creating a free space inside the mesh for unobstructed suction.

With reference now to FIGS. 3A-C therein are illustrated some of the main specifications of the funnel 1 according to an embodiment. Table 1 indicates the main specifications of the funnel 1. Table 2 indicates the measuring method used for calculating such parameters.

TABLE 1

Main specifications of the funnel

| | | Example | Range | Big Ref. | Small Ref. |
|---|---|---|---|---|---|
| Shape parameters | OD sec 20 [mm] | 6 | 3.5-6 | 5.2 | Approx. 4.1 |
| | OD sec 32 [mm] | catheter OD | 1-2 | 1.65 | 1.65 |
| | L sec 20 [mm] | 15 | 4-40 | 9 | 4-8 |
| | α sec 31 [°] | 45 | 15-45 | 31 | 20 |
| | L sec 32 [mm] | 2 | 1-10 | 3.5 | 3 |
| Braiding parameters | Wire OD [μm] | 50 | 40-60 | 51 | 51-58 |
| | Wire number | 48 | 24-48 | 48 | 24-36 |
| | β sec 20 [°] | 60 | 50-65 | 55 | 65 |
| | β sec 32 [°] | 20 | 15-50 | 45 | 45 |

Table 1 shows the parameters for particular embodiments. In an embodiment, the parameters of the funnel 1 are such indicated in Table 1 for a big blood vessel ("Big Ref") of e.g. 4.5 mm diameter, such as the final part of the carotid artery or the carotid siphon. In another embodiment, the parameters of the funnel 1 are such indicated in Table 1 for a small blood vessel ("Small Ref") of e.g. 2.5 mm diameter, such as the Internal Carotid Artery (ICA) or the Middle Cerebral Artery (MCA).

TABLE 2

Measuring methods used for calculating the different parameters.

| Parameter | Measuring method |
|---|---|
| OD sec 20 [mm] | The mandrel on which the funnel is meshed is measured. It is a solid piece with the same shape as the stent. The final diameter is determined by measuring the diameter of the solid piece and adding 4 times the diameter of the helicoidal filaments/wires. |
| OD sec 32 [mm] | Same as before |
| L sec 20 [mm] | Same as before |
| α sec 31 [°] | Same as before |
| L sec 32 [mm] | Once the funnel has been meshed, it is placed on a tool that determines where the excess length should be cut. |
| Wire OD [μm] | It is measured with a precision measuring instrument. |
| Wire number | Alternative 1: Counting the number of distal loops and multiplying by 2. Alternative 2: Counting the number of reels used for meshing |
| β sec 20 [°] | Alternative 1: Measuring the number of wire crossings in a given length measured in the axial direction. Alternative 2: If the mandrel is manufactured with grooves so that during the meshing the wires are inserted inside, and the manufacturing is improved, it is simply measured that the mandrel is manufactured with the appropriate parameters. |
| β sec 32 [°] | Same as before. |

As mentioned, the funnel 1 may be in two configurations: in a retracted form (or compressed state) inside the delivery catheter 3 or guide catheter, and in an extended and expanded (deployed) form outside the delivery catheter 3 or guide catheter. The parameters specified herein relate to the funnel 1 in its natural (relaxed) form, i.e., its extended and expanded (deployed) position. The segment 10 may include radiopaque markers made of platinum, tungsten, barium derivatives, gold, iridium, among others, at its distal end 11 and/or other strategic points within the mesh 13 which allow a physician to know the precise location of the funnel 1 while using fluoroscopy. The radiopaque material can be deposited on the helicoidal filaments once manufactured (if the funnel 1 has a coating, the material may also be dispersed on the surface of the coating). Alternative possibilities to confer radiopacity to the segment 10 are using helicoidal filaments of different material and opacity grade (e.g., Nitinol and Platinum). In an embodiment, Nitinol wires with a Platinum core are used. Likewise, the delivery catheter 3 may also include radiopaque markers.

Moreover, the segment 10 may have a coating, for example covering the first section 20, the second section 30, or covering the whole segment 10. In another embodiment, the coating is disposed over the first sub-section 31 of the second section 30. In the embodiments of FIGS. 1 and 2, although not seen, the coating goes from the closed loops 23 to sub-section 32. In one embodiment, the coating is applied about attachment of segment 10 to the funnel catheter 2 by dipping segment 10 into a liquid polymer, therefore allowing the polymer to solidify. Optionally, a mandrel may be disposed inside the mesh 13 of segment 10 when it is dipped into the polymeric coating material. Alternatively, the coating material may be sprayed onto the mesh 13. In other alternative embodiments, the coating may be applied before attaching segment 10 to the funnel catheter 2. In such embodiments, the coating does not reach the proximal end 12 of sub-section 32, but there is an uncoated space between the helicoidal filaments, leaving them free to allow assembly with the funnel catheter 2.

The coating prevents damage to the arteries, avoiding direct contact with the helicoidal filaments. Moreover, the coating provides a watertight compartment so that the thrombus THR can be sucked in and protected during removal. In an embodiment, to apply the coating, the mesh 13 is attached to the delivery catheter 3 and then the coating is applied.

An interior or exterior glaze can be also applied to the coating to improve its properties. By applying a hydrophilic or hydrophobic coating to the exterior surface of the segment 10, the exterior surface can be more easily displaced into the carrier and through the blood vessel by reducing the coefficient of friction. In the same way, by applying a treatment in the interior surface of the segment 10 an adhesion effect that retains the thrombus THR once it is inside can be achieved. The coating is made of an elastic material. In one embodiment, the funnel 1 coating is silicone. Alternatively, polyurethanes or other types of plastic materials can be used. A blend of polyurethane and silicone may also be employed.

To achieve the double behavior of the coating (lubricious on the exterior surface of segment 10 and tacky or rough inside), the coating can be treated by the addition of a material as explained or can have constitutively such features by the structure of the mesh itself.

The coating can include holes to avoid collapse of the segment 10. Such holes may be formed after the coating has been applied by perforating the coating.

The dimensions of segment 10 depend on the dimensions of the blood vessel in which it will be used to capture a thrombus THR. The dimensions of the sub-sections of segment 10 and the braid angles of the mesh help segment 10 provide a reduced radially outward force when compressed into the delivery catheter 3 and sufficient outward force when expanded to avoid collapse from the blood pressure. FIG. 4 illustrates a possible work curve of one embodiment of the segment 10. Y-axis defines the device pressure (mmHg) whereas X-axis defines the diameter of the arteries (mm). The horizontal dotted line marks the blood pressure limit. In some embodiments, the diameter range of the arteries in which the funnel 1 of this invention may be used is 2 to 5 mm. The segment 10 is designed so that it can expand without being blocked by the artery working in a standard range of 2 to 5 mm and so that it can cope with a blood pressure greater than 200 mmHg. As shown by FIG. 4, this embodiment is not designed to be compressed to a diameter less than 2 mm. Compression of the segment 10 within the delivery catheter 3 may result in radially outward forces high enough to inhibit advancement of the funnel 1 within the carrier.

Figure 24:
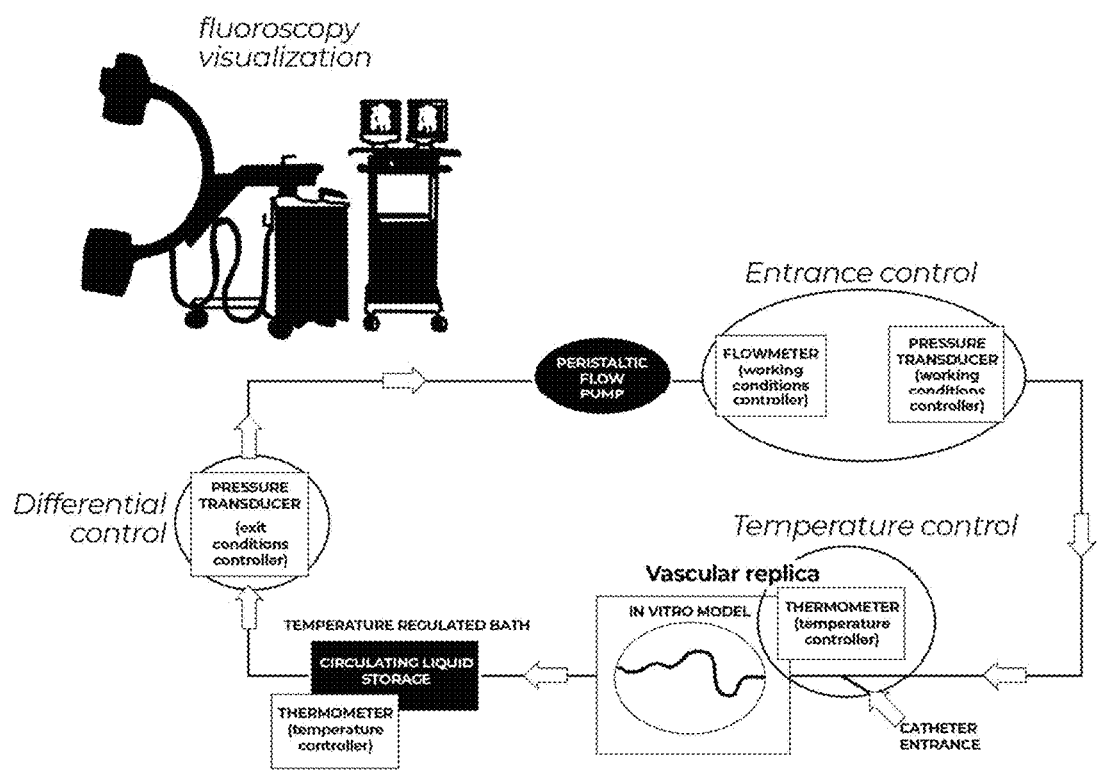
FIG. 24 shows a diagram illustrating an automated thrombectomy system according to an embodiment of the present invention.

Some embodiments of the invention may be automated for used in traditional (hospital) and non-traditional (nursing home, assisted care facility) environments which may allow for greater deployment and usage of the ANCD and hasten the removal of thrombus THR, thus significantly improving patient outcomes, as flow may be restored (e.g., to critical areas of the brain) within much shorter times. One such automated device is shown in FIG. 24 and described in WO2016113047 and WO2020099386. In use of the ANCD, segment 10 and the funnel catheter 2 to which it is attached are advanced through the delivery catheter 3 to a thrombus site within a blood vessel of the patient. During advancement in the delivery catheter 3, the segment 10 is in a delivery configuration in which the first and second sets of helicoidal filaments form a first distally facing angle with respect to each other. When segment 10 emerges from the delivery catheter 3, it begins to self-expand to a deployment configuration. In embodiments in which the mesh 13 forms closed loops at the distal end of segment 10, the spring action of the closed loops of the helicoidal filaments helps the first section 20 expand into apposition with the blood vessel proximate to the thrombus site. In the deployment configuration, the first and second sets of helicoidal filaments form a second distally facing angle less than the first angle (i.e., the filaments are less longitudinally aligned in the deployment configuration than they were in the delivery configuration). Sub-section 31 also self-expands to a conical or funnel shape. The distal end of sub-section 31 helps support the proximal end of section 20 in its deployment configuration.

The non-permeable coating allows the funnel to reduce or stop the flow. The optional holes through the coating permit a small amount of blood to pass through the funnel 1 to avoid collapse of sub-section 31 caused by the blood pressure and also by the difference of pressure between the blood pressure (externally) and the vacuum applied (internally). Once blood flow has been reduced or stopped, suction may be applied through the funnel catheter 2 to the interior spaces of sub-section 31 and section 20 to aspirate the thrombus THR into section 20. Funnel 1 and the captured thrombus THR may then be removed from the patient. In the capture configuration (i.e., when the thrombus THR is inside), the first and second sets of filaments form a third distally-facing angle less than the first distally-faced angle (i.e., the filaments become more longitudinally aligned) as the funnel 1 assumes a longer and smaller diameter shape.

Figure 5:
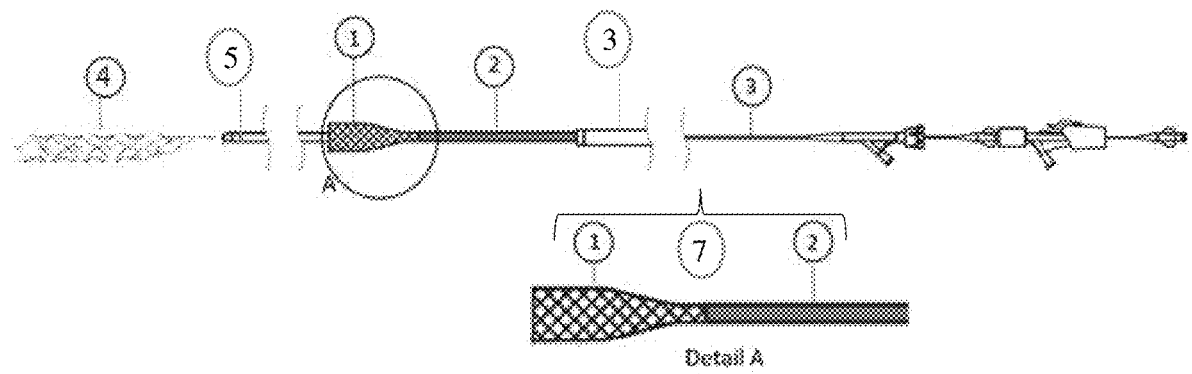
FIG. 5 is a scheme of an embodiment of the thrombectomy system.

With reference to FIG. 5, therein it is illustrated a scheme of an expanded configuration of the thrombectomy system, which in this embodiment includes a funnel 1, a funnel catheter 2 connected to the funnel 1, a guide catheter or a delivery catheter 3; a clot-capture element 4 and a microcatheter 5. Detail A shows a scheme of an expandable-tip catheter 7 comprising the funnel 1 and the catheter 2.

When the occlusion site is in the cerebral vasculature, it may not be desirable or even possible to advance the delivery catheter and funnel through the tortuous carotid siphon. We have discovered that unexpectedly good recanalization results can be achieved by deploying the funnel in the internal carotid artery at or proximal to the distal end of the carotid siphon (e.g., in or near the apex of the carotid siphon), or even proximal to the proximal end of the carotid siphon, and advancing a clot-mobilizer and/or a distal access catheter further distally to the occlusion site in the cerebral vasculature beyond the carotid siphon to capture and retrieve the thrombus.

Figure 6:
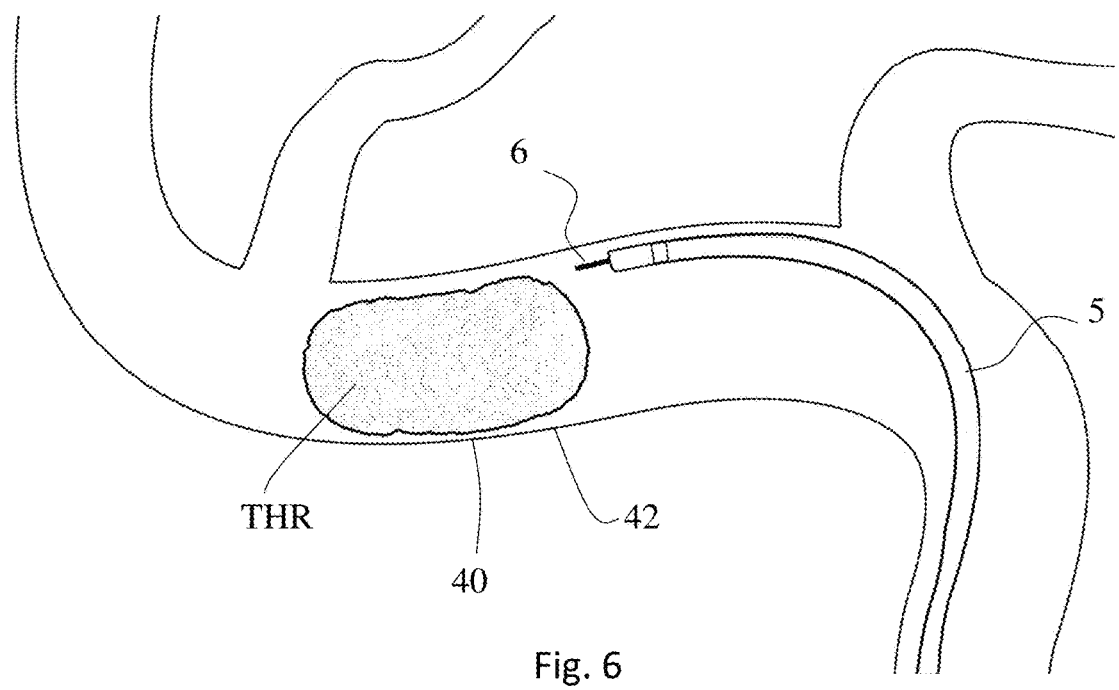
FIGS. 6-13 show the steps of one method of extracting a thrombus from a thrombus site in a blood vessel of a patient using the system of the invention.
Figure 7:
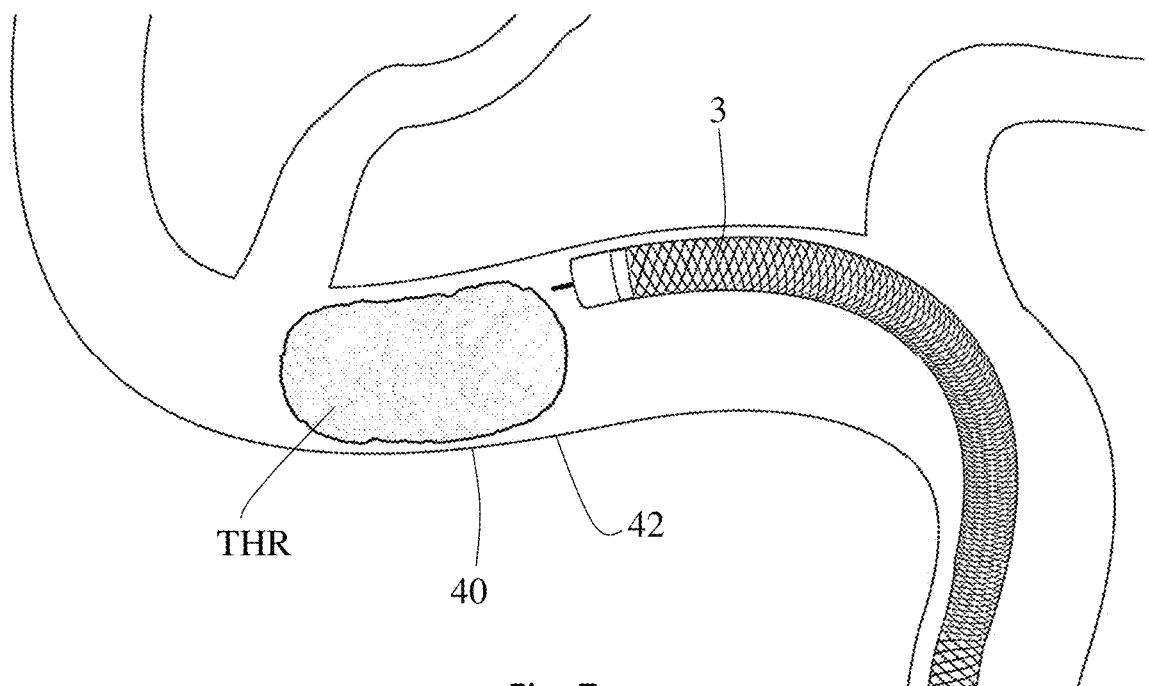
Figure 8:
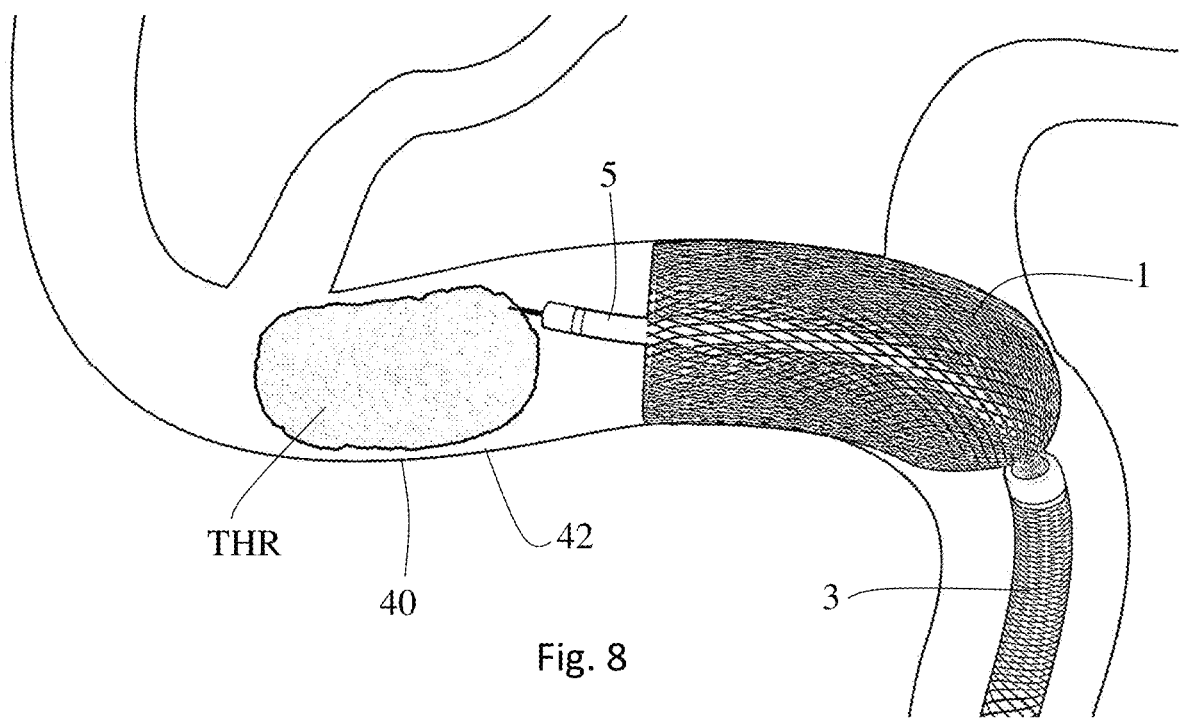
Figure 9:
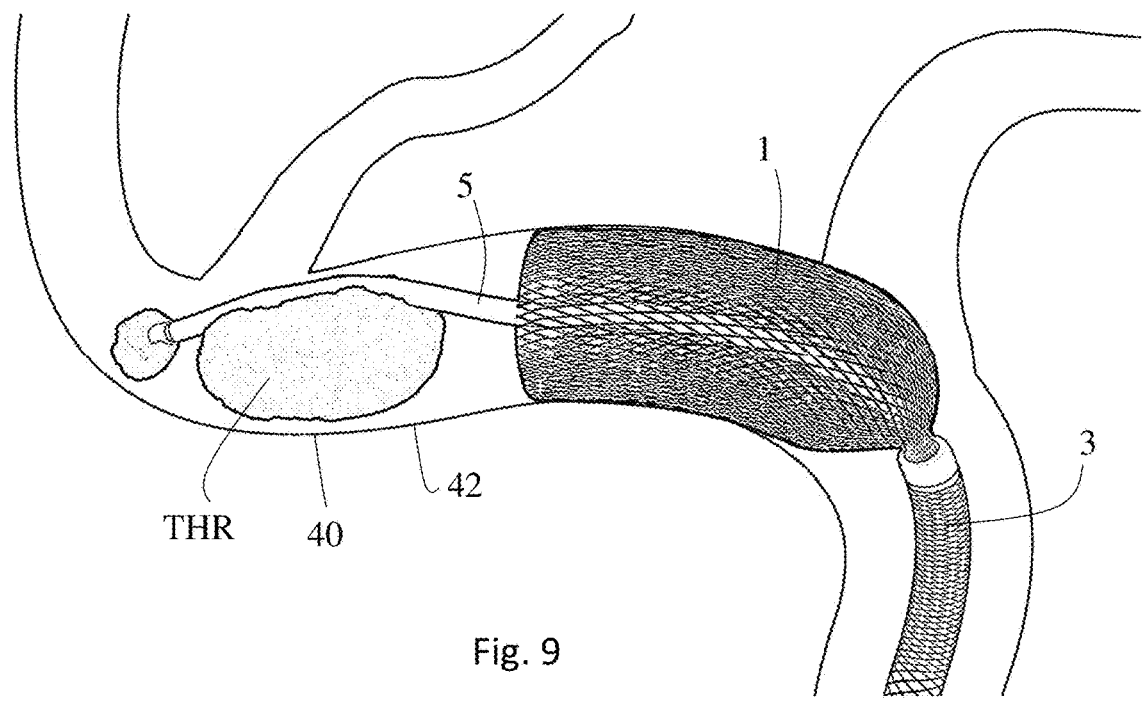
Figure 10:
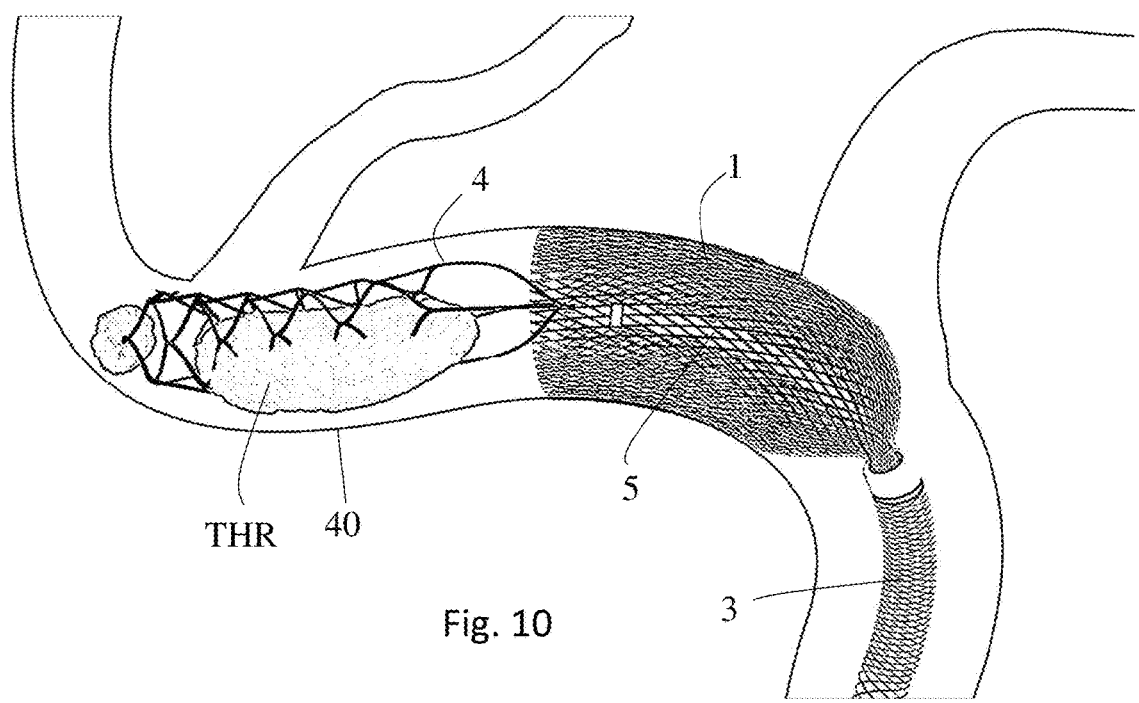
Figure 11:
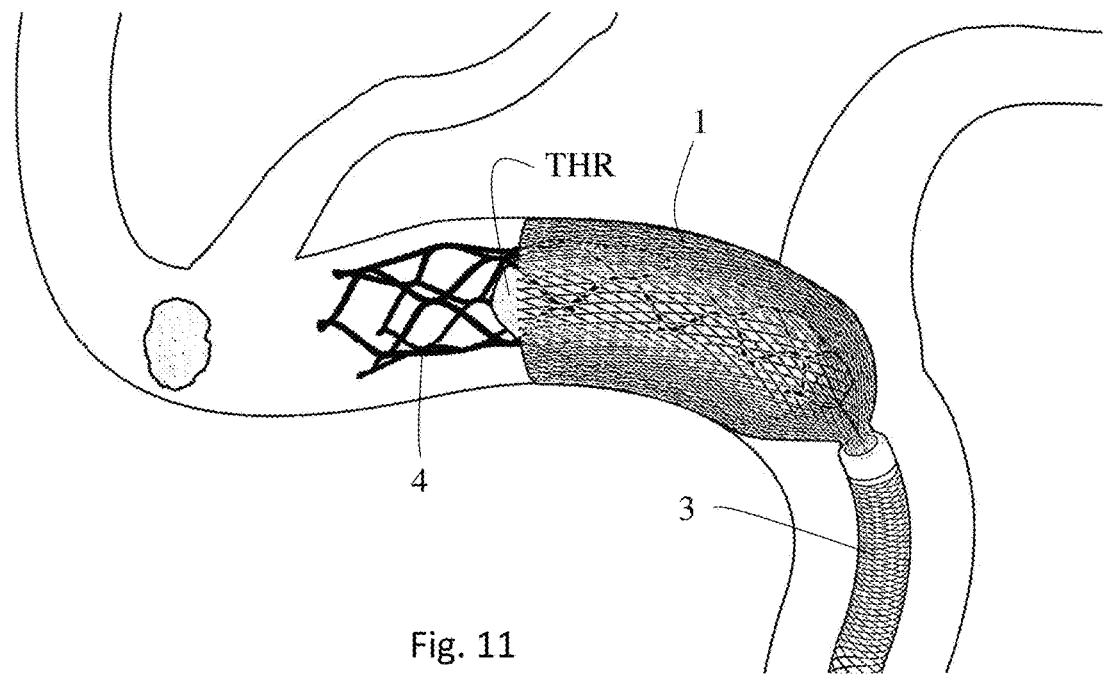
Figure 12:
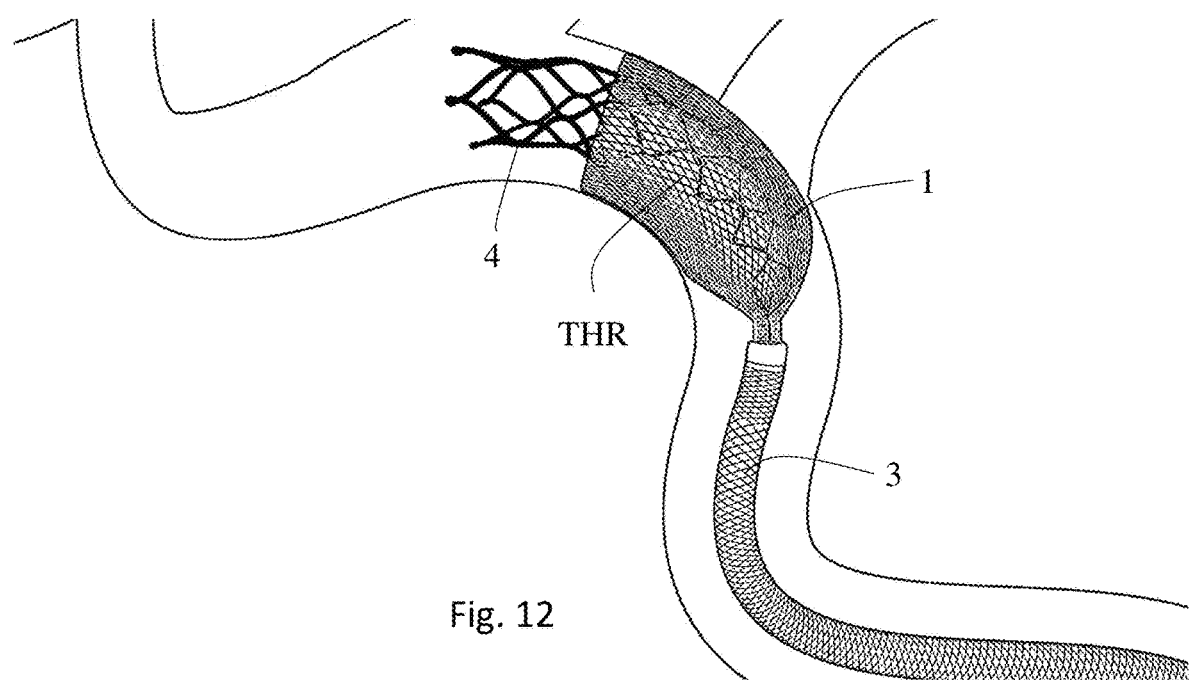
Figure 13:
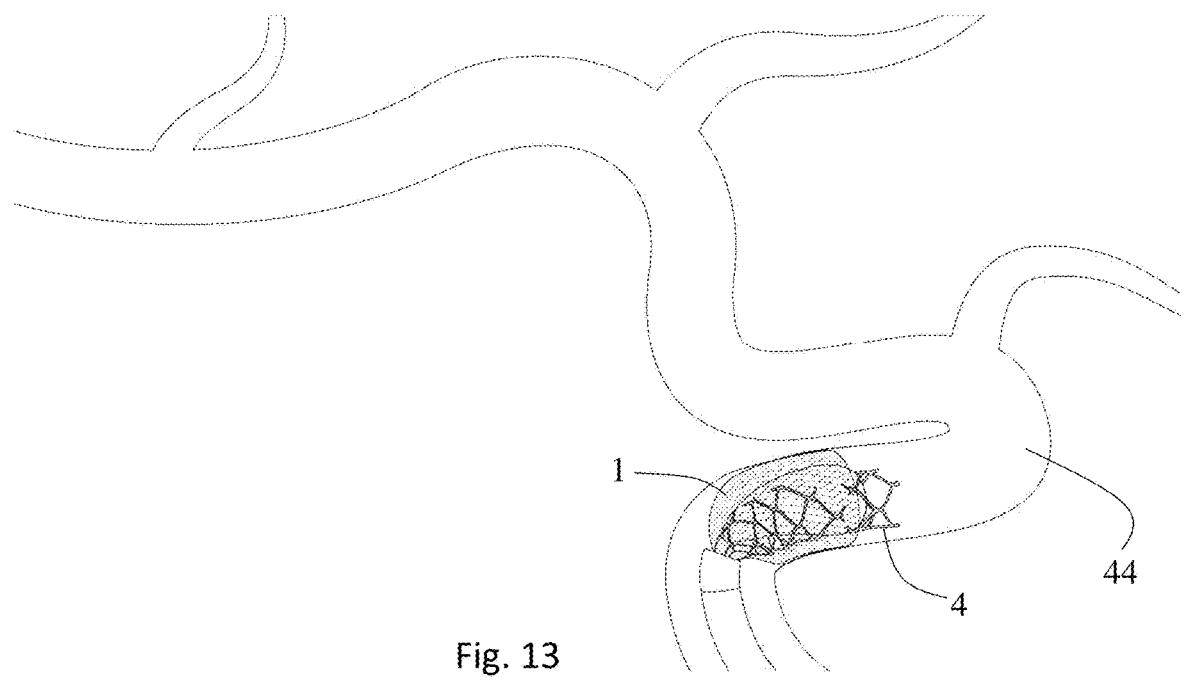

FIGS. 6-13 show steps of a method of extracting a thrombus THR from a thrombus site 40 in a cerebral blood vessel 42 of a patient using the system of the invention. First, a guide wire 6 is advanced to the thrombus THR, and a microcatheter 5 is advanced over the guide wire 6, as shown in FIG. 6, and the delivery catheter 3 containing the expandable-tip catheter (not shown) is advanced over a guide wire 6 and the microcatheter 5 to a position just proximal to the thrombus site 40, as shown in FIG. 7. (Alternatively, the delivery catheter 3, microcatheter 5, and expandable-tip catheter 7 may be advanced together over guide wire 6.) Once the delivery catheter 3 reaches its position, it is withdrawn as the expandable-tip catheter is held stationary to expose and deploy through self-expansion the coated funnel 1 at the mouth of the expandable-tip catheter. The funnel 1 self-expands to the diameter of the vessel 42, as shown in FIG. 8. The non-permeable coating on the funnel, and the outward radial force applied by the mesh of the funnel 1, seals funnel 1 against the inner wall of the vessel 42 to stop or significantly slow blood flow past the funnel. Once the mouth of the funnel 1 is opened, the microcatheter 5 is advanced into and optionally through the thrombus THR, as shown in FIG. 9. Then the microcatheter 5 is withdrawn while a pusher (not shown) extending proximally from the proximal end of clot-mobilizer 4 holds clot-mobilizer 4 in place to self-expand and deploy the clot-mobilizer 4 into the thrombus, capturing some or all of the thrombus material from the thrombus (FIG. 10). The clot-mobilizer 4 is withdrawn with the pusher to drag the thrombus material to the funnel 1 mouth while suction is applied to the funnel catheter 2 (e.g., by means of a syringe, not shown) to aspirate the thrombus material into the funnel (FIG. 11). In some embodiments, suction is not applied to the funnel 1 until the proximal end of the clot-mobilizer 4 enters the funnel. Finally, the thrombus material is engaged in the funnel 1 (FIG. 12), and the system is removed proximally through the carotid siphon 44 and the proximal vasculature for removal from the patient (FIG. 13). The mesh of funnel 1 lengthens as it narrows to retain the thrombus material within it as it traverses the vasculature during removal from the patient.

FIGS. 14-23 show another method of the present invention using the thrombectomy system described above. In some instances, the clinician removing a clot from a cerebral artery will choose to cease advancement of the delivery catheter, or the guide catheter, before reaching the clot. For example, in some patients it may not be possible to advance the delivery catheter through some or all of the turns of the carotid siphon, or it may take so long to navigate the delivery catheter through the carotid siphon that the overall procedure time will be unnecessarily extended. In such situations, the clinician may choose to deploy the funnel at a site proximal to the distal end of the carotid siphon, or proximal to the apex of the carotid siphon, or even proximal to the proximal end of the carotid siphon. The microcatheter containing the clot-mobilizer, which has a much smaller diameter, can then be advanced from the funnel to the clot.

Figure 14:
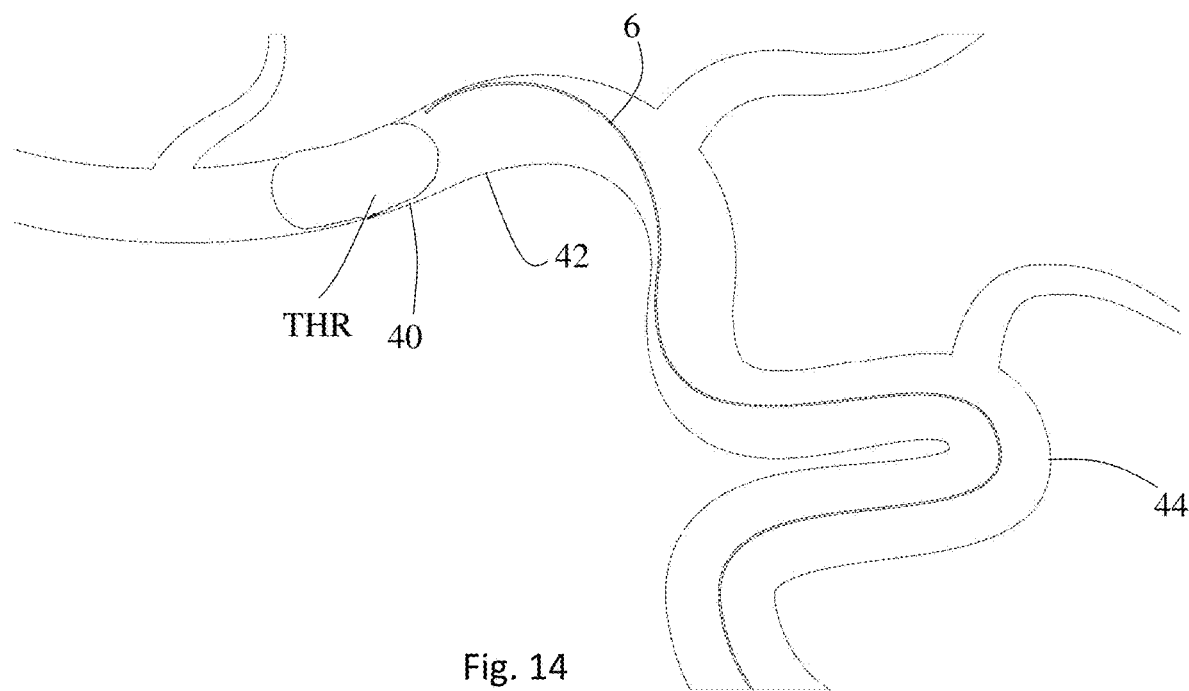
FIGS. 14-23 show the steps of another method of extracting a thrombus from a thrombus site in a blood vessel of a patient using the system of the invention.
Figure 15:
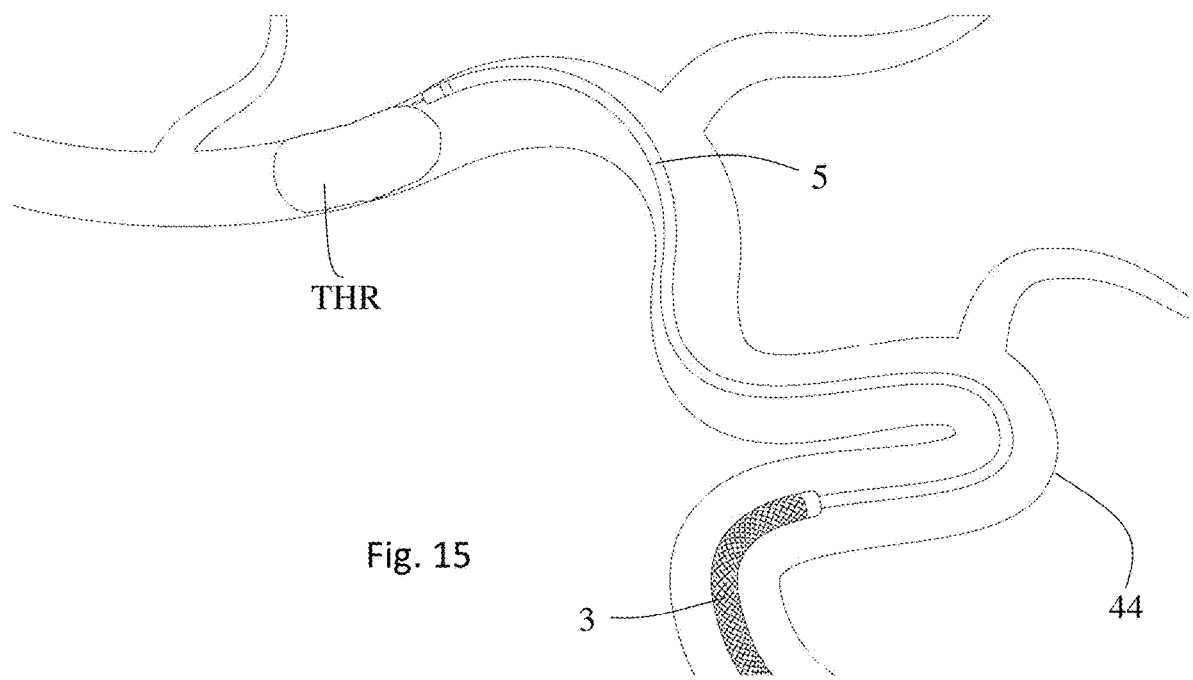
Figure 16:
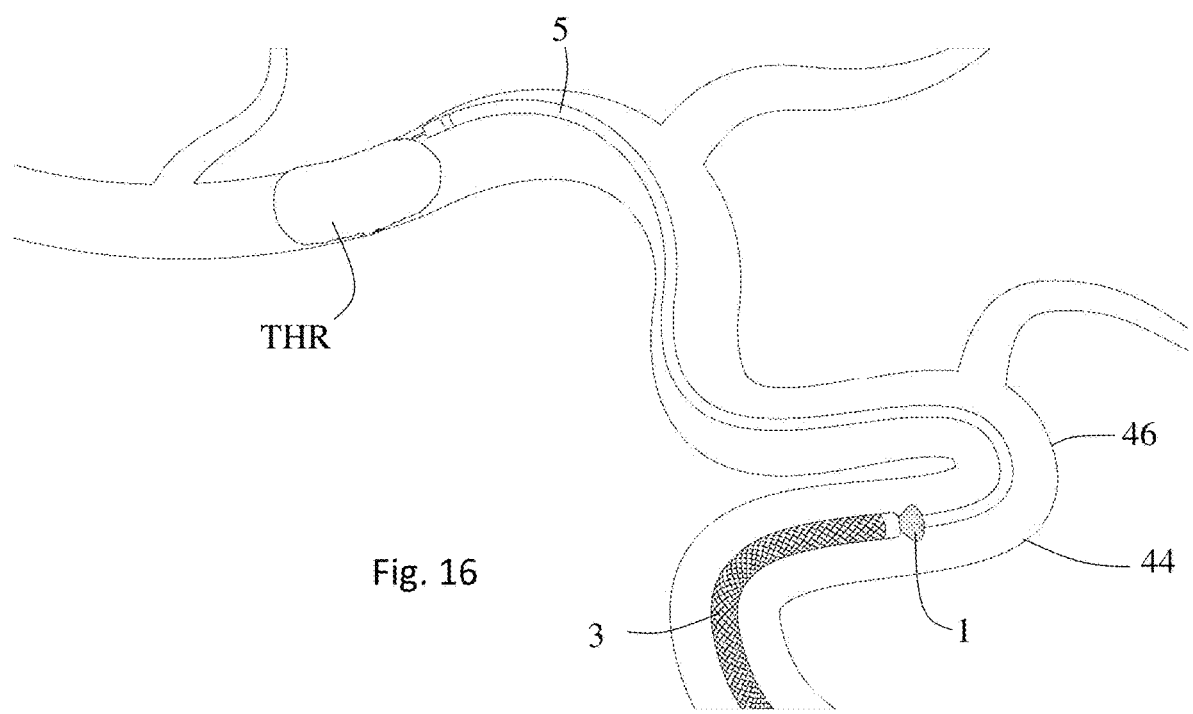
Figure 17:
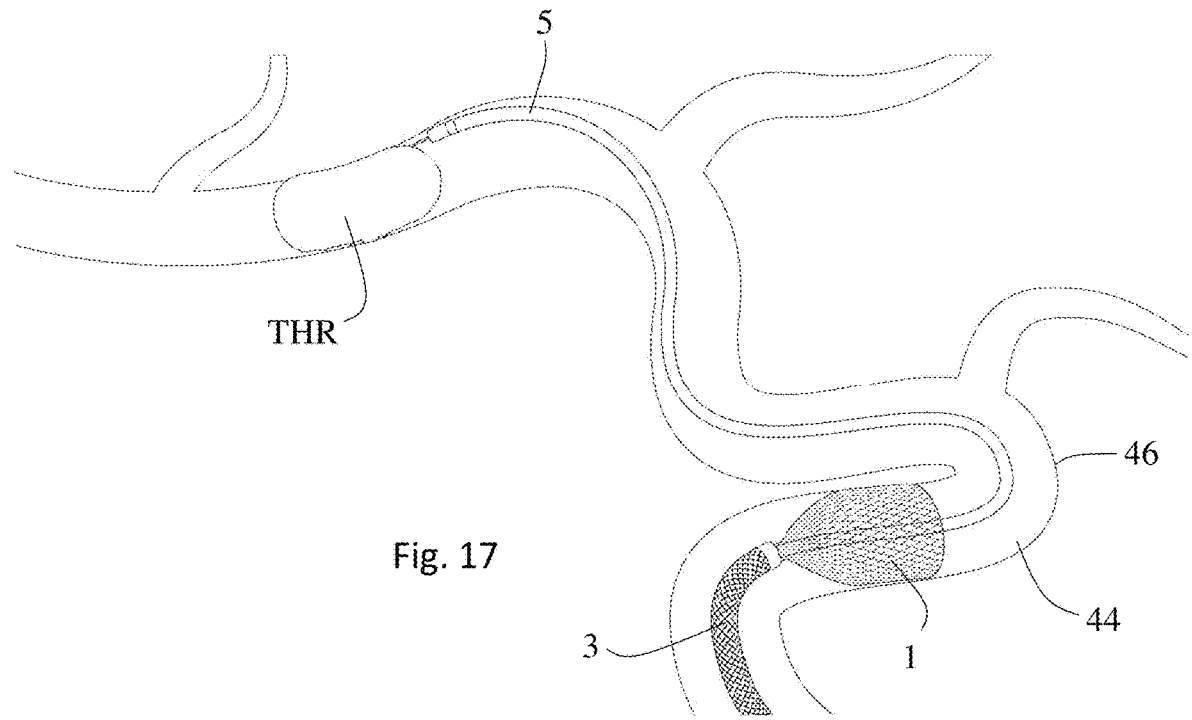
Figure 18:
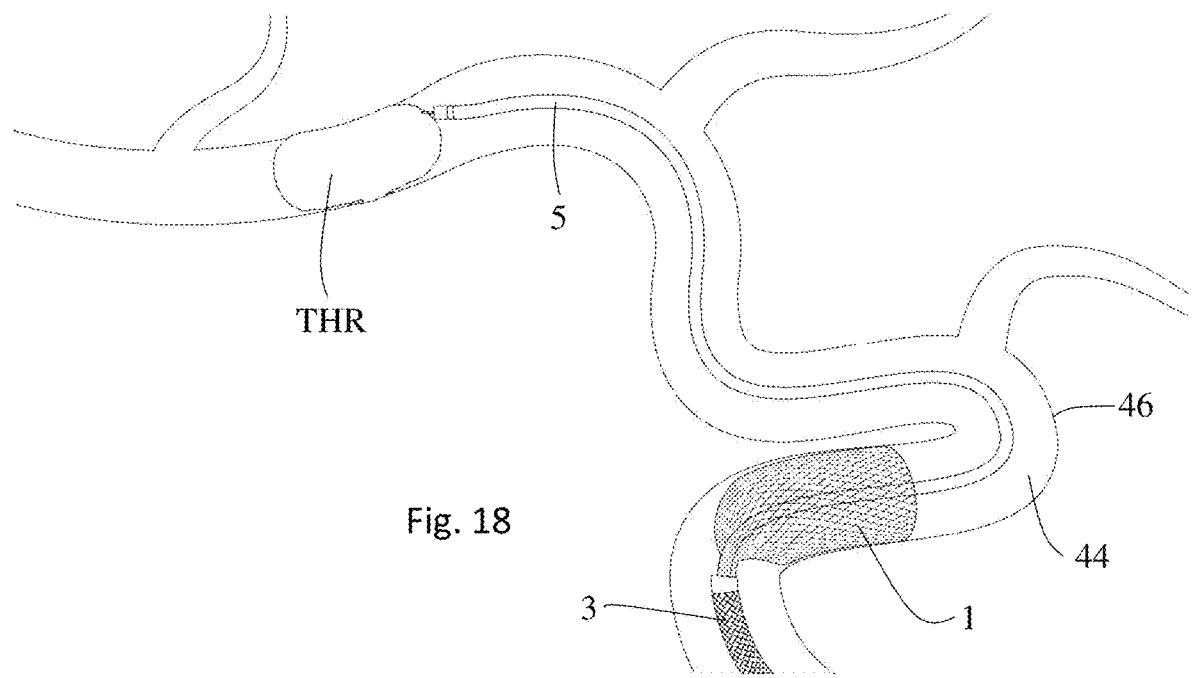
Figure 19:
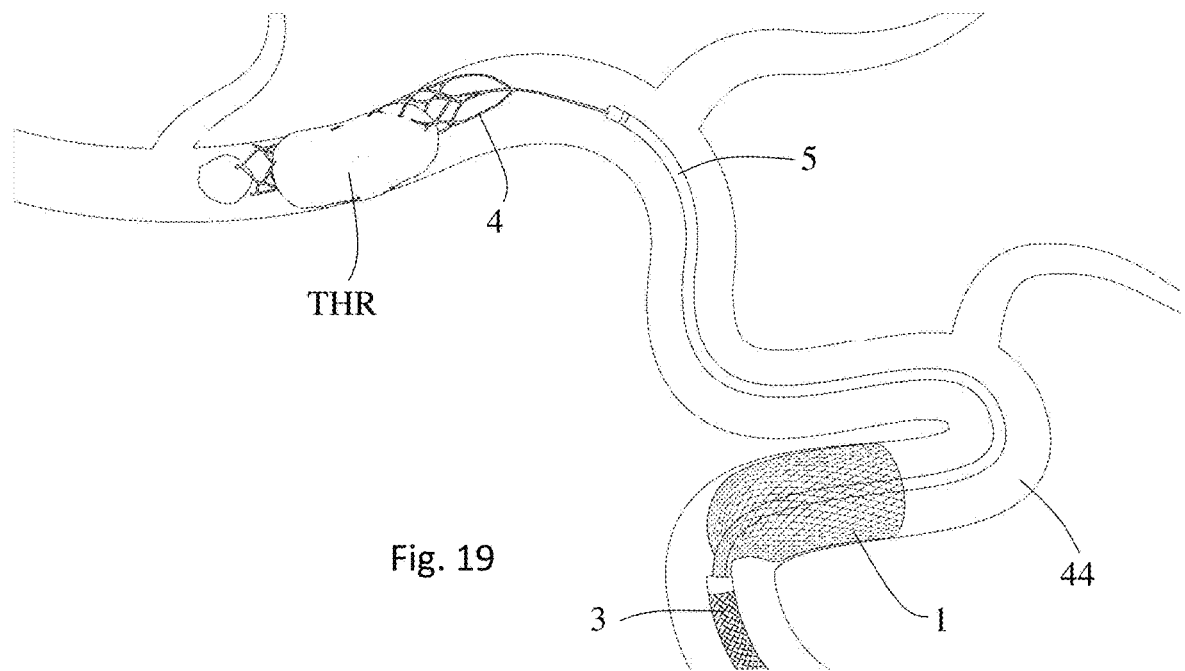
Figure 20:
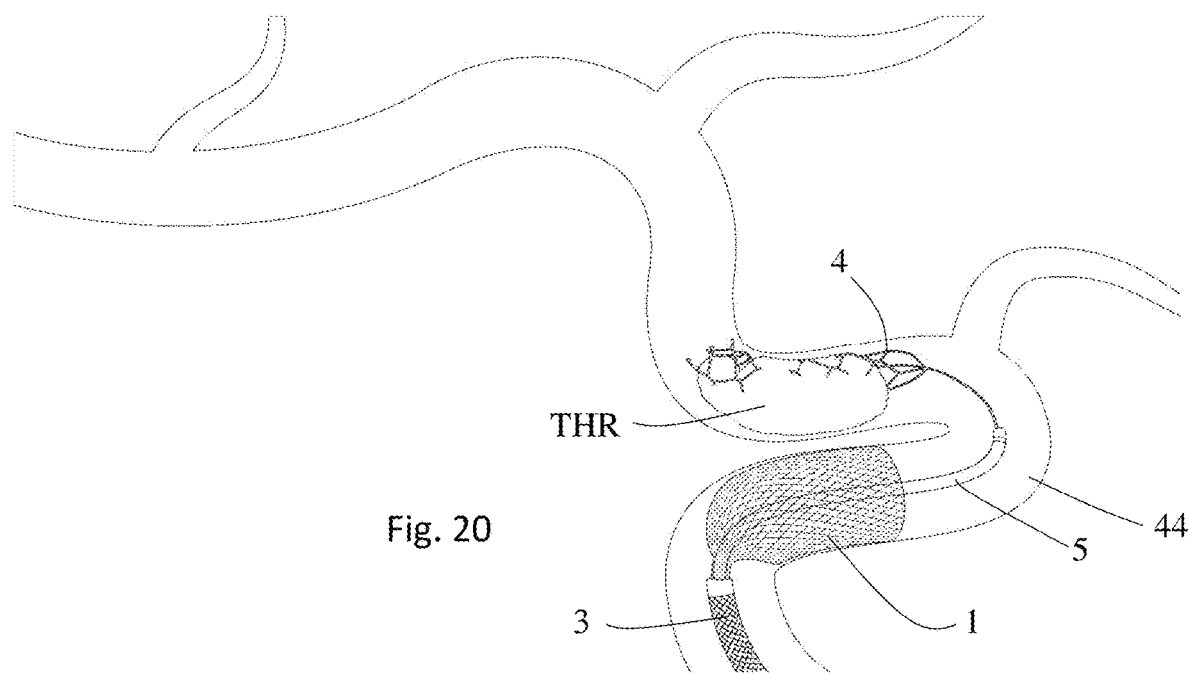
Figure 21:
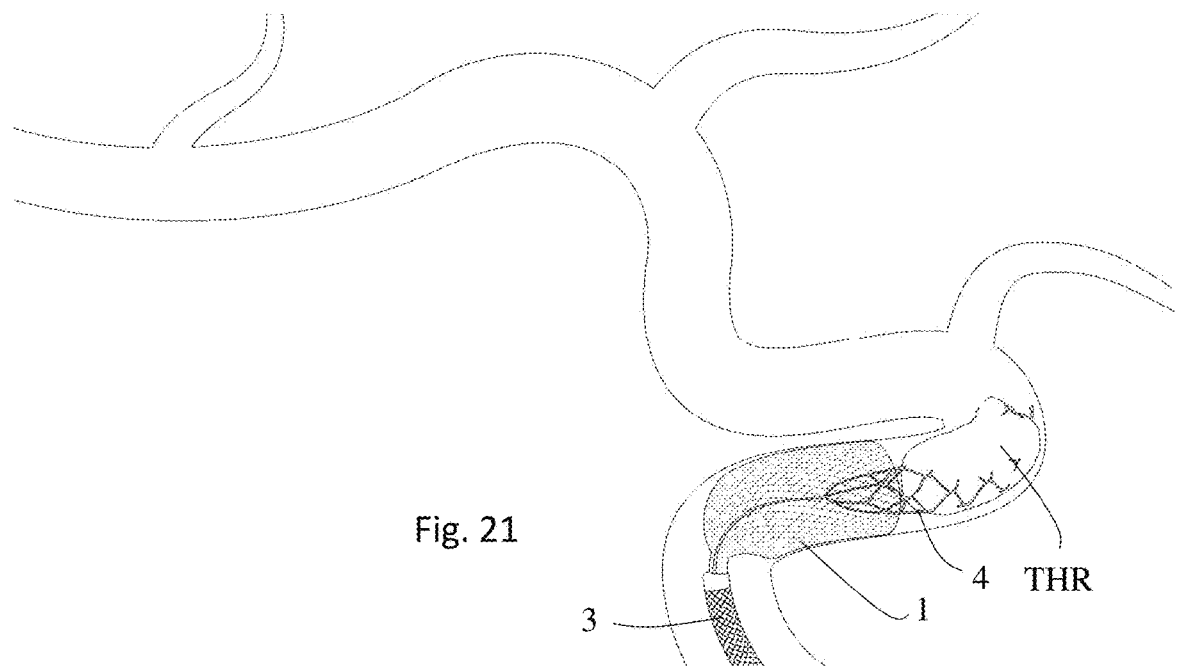
Figure 22:
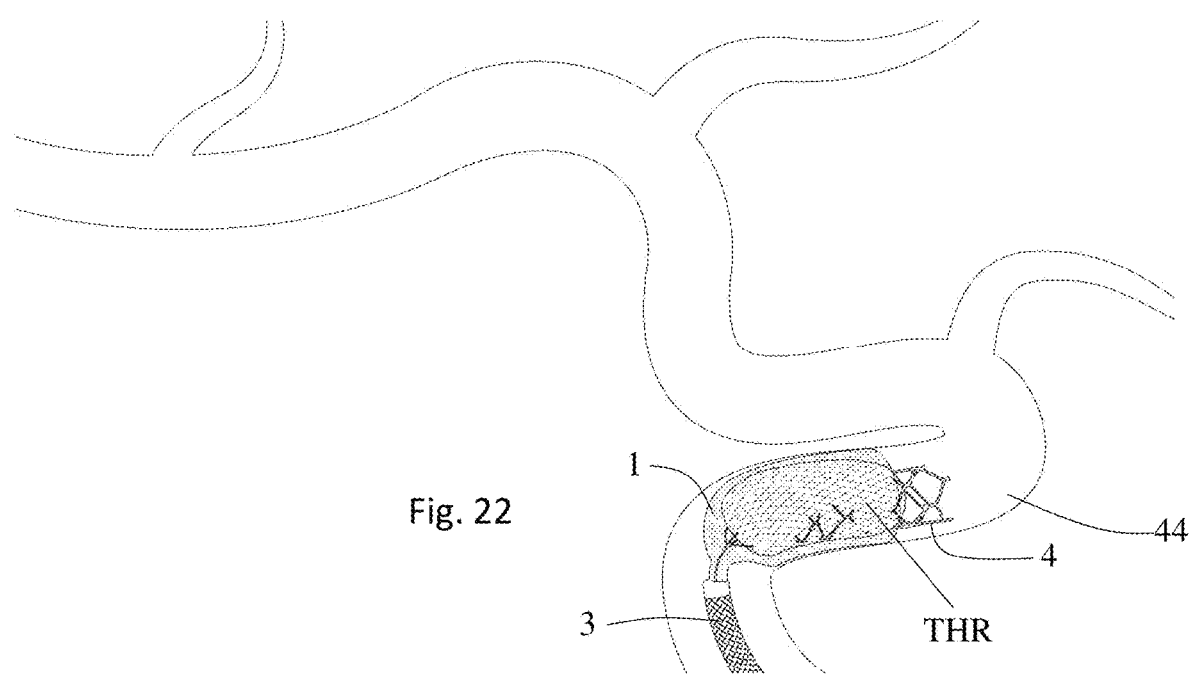
Figure 23:
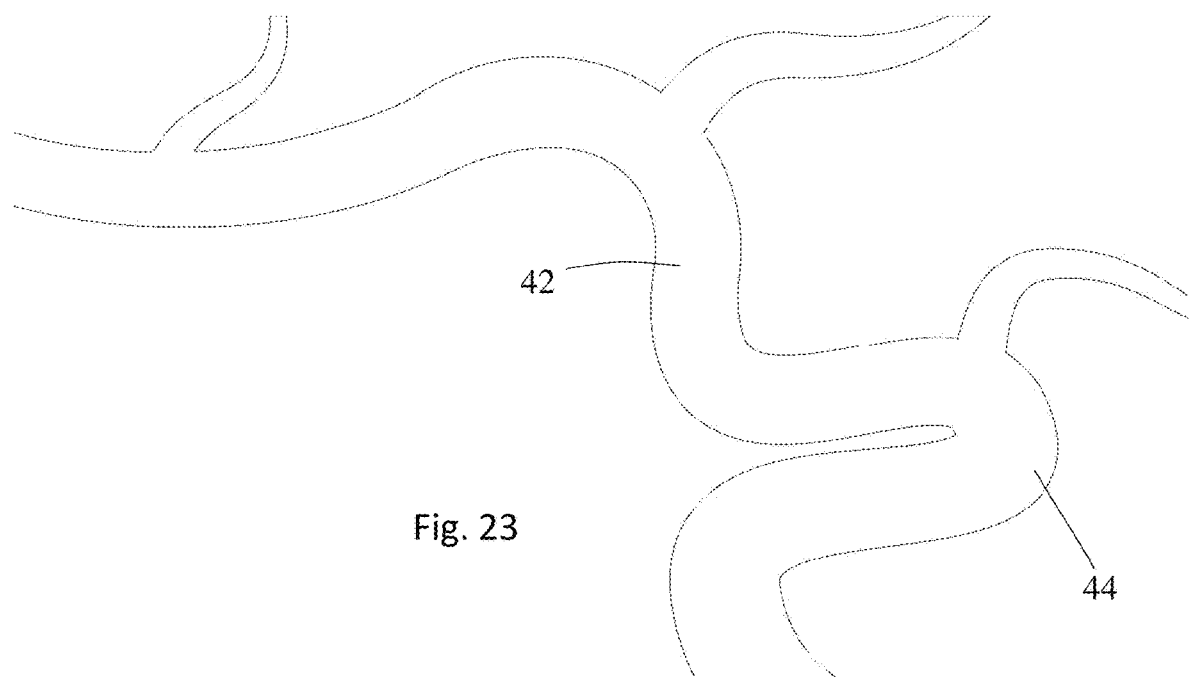

FIG. 14 shows a thrombus THR at a thrombus site 40 in a cerebral vessel 42 distal to the carotid siphon 44. A guide wire 6 has been advanced to a position in cerebral vessel 42 just proximal to the thrombus site 40. As shown in FIG. 15, the delivery catheter 3 is advanced to a position within the carotid siphon 44 and proximal to the apex 46 of the carotid siphon, while microcatheter 5 has been advanced over guide wire 6 to the thrombus site 40. The coated funnel 1 is deployed within the carotid siphon to self-expand to the diameter of the vessel, proximal to the apex 46, as shown in FIGS. 16-18. In some embodiments, the funnel is deployed into contact with the inner wall of the carotid artery proximal to the proximal end of the carotid siphon (not shown). The non-permeable coating on the funnel 1, and the outward radial force applied by the mesh of the funnel 1, seals funnel 1 against the inner wall of the vessel to stop or significantly slow blood flow past the funnel. The clot-mobilizer 4 is then deployed in the manner described above to capture thrombus material, as shown in FIG. 19. In an embodiment, the clot-mobilizer is deployed (i.e., expanded) into contact with an arterial wall. After capturing the thrombus material, the clot-mobilizer 4 and the microcatheter 5 are drawn proximally toward the funnel 1, as shown in FIG. 20. Optionally, to reduce the risk of collapsing the funnel when suction is applied, suction is applied to the funnel catheter and funnel 1 when the proximal end of clot-mobilizer 4 begins to enter funnel 1, as shown in FIG. 21. In some embodiments, the suction begins when the clot-mobilizer is disposed adjacent to a distal end of the funnel 1. In another embodiment, the suction begins when the clot-mobilizer moves proximally at least part way into the funnel 1. The clot-mobilizer and captured thrombus material are then held within funnel 1 during removal. The mesh of funnel 1 lengthens as it narrows to retain the thrombus material within it as it traverses the vasculature during removal from the patient.

In some methods of removing a clot from the cerebral vasculature, a guide catheter or sheath is inserted into the patient's femoral artery and advanced into the aorta and the carotid artery, and the delivery catheter, the funnel catheter and the microcatheter with the clot-mobilizer are advanced through the guide catheter. The smaller diameter of the delivery catheter enables it to be advanced further into the cerebral vasculature toward the thrombus site.

In other methods, introduction sites other than the femoral artery may be used, such as the radial artery, the brachial artery, or the common carotid artery. The remaining steps of the method are the same as for the femoral artery entry method.

In some methods, the clot-mobilizer may be used as an anchor to assist in advancement of the guide catheter and/or delivery catheter, and funnel catheter. In this manner, the step of deploying the clot-mobilizer is performed before the step of expanding the funnel. For example, a microcatheter containing a clot-mobilizer such as a stent retriever can be advanced through tortuous vasculature to a position at or distal to a thrombus site, and the clot-mobilizer can be deployed to engage the blood vessel wall, e.g., by passing through the thrombus. Once deployed, the stent retriever acts as an anchor for the distal end of the microcatheter, and the microcatheter acts as a guide over which the delivery catheter, the funnel catheter or other catheters can be advanced through the tortuous vasculature.

As discussed above, guide catheters are sometimes used to advance tools to sites within the vasculature. A guide catheter may not be needed to advance the delivery catheter to the desired funnel deployment site. In some methods, therefore, the step of advancing the delivery catheter comprises advancing the delivery catheter to the internal carotid artery without using a guide catheter.

In other methods, the step of advancing the delivery catheter comprises advancing the delivery catheter through a guide catheter. In such methods, a guide catheter is inserted into the patient's vasculature at an access point, e.g., in a femoral artery or radial artery, and advanced toward the thrombus site, e.g., into the aortic arch, ostium of the common carotid artery or internal carotid artery. The smaller diameter delivery catheter, in which the funnel, funnel catheter, clot-mobilizer and/or distal access catheter are disposed, can then be advanced out of the guide catheter into the internal carotid artery.

In some methods, the desired funnel deployment site can be reached by a guide catheter. In such situations, a guide catheter can be used as the catheter through which the funnel catheter is advanced and from which the funnel is deployed.

EXAMPLES

Example 1

1. Study Objectives

This study aimed to assess the performance of ANCD 5.2*9 mm prototype 2018 (hereinafter referred as ANCD). ANCD 5.2*9 mm prototype 2018 is an expandable-tip aspiration catheter built using a DFT (Nitinol/platinum) braided structure covered with silicone as defined below. The performances were evaluated in an in vitro 3D simulation model, a cerebrovascular model of the intracranial circulation that simulates the carotid and cerebral physiological blood flow, pressure and vessel anatomy including an occlusive ex vivo clot analog.

TABLE 3

| ANCD 5.2 * 9 mm prototype 2018 | | |
|---|---|---|
| Shape parameters | OD sec 20 [mm] | 5.2 |
| | OD sec 32 [mm] | 1.65 |
| | L sec 20 [mm] | 9 |
| | α sec 31 [°] | 31 |
| | L sec 32 [mm] | 3.5 |
| Braiding parameters | Wire OD [µm] | 51 |
| | Wire number | 48 |
| | β sec 20 [°] | 55 |
| | β sec 32 [°] | 45 |

Specifically, this study aimed to assess the efficacy of ANCD in combination with stent retrievers in terms of the rate of revascularization and rate of clot embolization.

2. Materials and Methods 2.1 Samples

The ANCD devices used in the study were the following (Table 4):

| Funnel Catheter | Funnel Model | Funnel Reference | Delivery Catheter |
|---|---|---|---|
| Group 10/ Sample 8 | 5.2 * 9 mm | ZA00583-03 | Coiled delivery (new)/ group 10/sample 8 |
| lot 945034 sample 10 | 5.2 * 9 mm | ZA00599-10 | Coiled delivery (new)/ group 10/sample 8 |
| Sample 2-IVT efficacy | 5.2 * 9 mm | ZA00600-02 | Sample 3-IVT ANCD Compatibility |
| Sample 5-IVT efficacy | 5.2 * 9 mm | ZA00600-05 | Sample 3-IVT ANCD Compatibility |
| Sample 5-IVT efficacy | 5.2 * 9 mm | ZA00601-06 | Sample 3-IVT efficacy |
| sample 3-IVT. Efficacy IVT SAB | 5.2 * 9 mm | ZA00615-03 | Sample 4-IVT compatibility |
| Group 10/ Sample 8 | 5.2 * 9 mm | ZA00599-02 | Sample 4-IVT compatibility |

The marketed devices are shown below (Table 5):

| Device type | Name | | Company |
|---|---|---|---|
| Thrombectomy devices | Stent Retrievers | Solitaire 4-6 × 20 mm | Medtronic |
| Neurovascular guide catheters | Guide catheter | Neuronmax 088 | Penumbra Inc |
| | Microcatheter | Rebar | Covidien |
| | Distal Access Catheters (DAC) | Navien | Covidien |
| | Balloon Guide Catheter (BGC) | Cello | Covidien |

2.2. Methodology

The study was carried out in the Animal Facility of the Institut de Recerca de Vall d'Hebrón (VHIR), Barcelona (Spain).

Mechanical thrombectomy with the ANCD device in combination with stent retrievers (Solitaire), and marketed devices (Solitaire with distal access catheter—"Solumbra-like"—, and Solitaire with balloon guide catheter) was simulated in the model cerebrovascular occlusion (including a clot analog). In addition, the performance of the ANCD device, including the navigability and the compatibility with different stent retrievers was also assessed in the presence and absence of clots.

The procedures were followed by low resolution fluoroscopy and assisted by trained technicians.

The model system of cerebrovasculature is composed of a human vascular replica and a physiologically relevant mock circulation flow loop, as described below.

Vascular Replica:

A three-dimensional in vitro model of the intracranial circulation was used as vascular replica.

Two models of vascular replica were used:

1. Vascular model Jacobs Institute: This model was designed based on patient vascular anatomy using CT-A imaging (50 patients) and then printed on a 3D printer (Jacobs Institute). The model closely resembles the human intracranial circulation in terms of curvature, diameter, and length, and consists of the internal carotid artery segment and middle cerebral artery branches (M1-M4 segments), bilateral A1 anterior cerebral artery segments connected to a single anterior cerebral artery, and a single posterior communicating artery (right side), thus allowing near complete circle of Willis circulation. In addition, a representative access vasculature compressing the aortic arc and the common carotid artery and cervical internal carotid are also included. The levels of tortuosity of the different sections of the vascular replica are moderate-severe, with an average tortuosity index of 4.752 and 2.332 for the intracranial and the access vasculature, respectively, creating a complete model with a tortuosity index of 7.084.

2. Vascular model UMASS (University of Massachusetts Medical School): A vascular replica of the entire circle of Willis with a severe ICA siphon in terms of curvature, diameter, and length was selected based on data from magnetic resonance angiograms of 20 patients and was built by using a small-batch manufacturing process. An ICA siphon with severe tortuosity is selected to offer challenging tortuosity for endovascular access. During the image post-processing, the 3D reconstruction of the vasculature is modified to rejoin the M2 and A2 divisions resulting in a single output from each vascular territory.

Two vascular replicas with different degree of tortuosity were used:
  (1) Moderate vascular model: the different sections of the vascular replica showed an average tortuosity index of 5.831 and 0.047 for the intracranial and the access vasculature, respectively, creating a complete model with a tortuosity index of 5.878.
  (2) Severe vascular model: the different sections of the vascular replica showed an average tortuosity index of 7.067 and 7.067 for the intracranial and the access vasculature, respectively, creating a complete model with a tortuosity index of 7.233.

Mock Circulation Flow Loop:

The model was connected to a peristaltic pump. Saline solution heated to 37° C. was circulated through the model using a peristaltic pump. The rate of flow into the full neurovascular model was set at 370-450 mL/min, values based in physiological flow rates. The pressure was also regulated to 180 mmHg, which is in the upper range of clinically representative blood pressure. Flow and pressure sensors were located in the entrance of the circuit, after the peristaltic pump output, while a second pressure sensor placed after the vascular replica calculates the differential pressure. A thermometer measures the fluid temperature in the mid zone. Intravascular devices were maneuvered under fluoroscopic guidance and angiographic images of the vessel were obtained with contrast media to identify the proper location of the target vessel.

2.3. Clot Analogs

For the assessment of the efficacy in clot retrieval (revascularization and embolization rates), soft red and fibrin rich clots were used to generate middle cerebral artery (MCA, M1) occlusions.

Porcine blood clots were fabricated in the VHIR. Soft red and fibrin rich clots were made as per Mokin et al 2016 and Duffy et al 2017 (Mokin M, et al., Stent retriever thrombectomy with the Cover accessory device versus proximal protection with a balloon guide catheter: in vitro stroke model comparison. J Neurointery Surg. 2016 vol. 8, pp. 413-7; Duffy S, et al., Novel methodology to replicate clot analogs with diverse composition in acute ischemic stroke. J Neurointery Surg. 2017 vol. 9, pp. 486-491) respectively:

Soft red clot: 4 ml of non-anticoagulated porcine blood was mixed with 32 mg of fibrinogen from bovine plasma (F8630, Sigma-Aldrich) and 1 unit of thrombin form bovine plasma (T4648, Sigma-Aldrich) for at least 3 min. The mixture was incubated at room temperature for at least 60 min.

Fibrin rich clot: Porcine blood was anticoagulated using sodium citrate solution (3.2%) immediately after collection. The whole blood constituents were subsequently separated using centrifugation (600 g, 15 min, 4° C.) and the extracted plasma was mixed with the red blood cells (RBCs) in a ratio of 9:1. Coagulation was initiated by the addition of calcium chloride (2.06%) and the clotted material was allowed to mature for 60 min at 37° C. The resultant clots consist of approximately 100% fibrin.

The clot (5×5×7 mm) was injected into the flow loop to form an MCA occlusion. Prior to initiating thrombectomy, complete occlusion with TICI 0 was required.

2.4. Procedure

Neuron Max 088 guide catheter (Penumbra) was placed in the cervical ICA and delivered over the guidewire which will be then gently advanced through the target vessel.

Thrombectomy Procedure (Clot Retrieval Procedure):

Marketed thrombectomy devices: A microcatheter was navigated over the wire across the occlusive clot. The guidewire was withdrawn followed by deployment of the stent retriever (Solitaire) for mechanical thrombectomy. During retriever retraction, continuous aspiration was applied during retrieval with the assistance of a 60 mL syringe.

ANCD in combination with stent retrievers: The ANCD was combined with the stent retriever to retrieve the clot: with the stented funnel deployed proximal to the occlusion, the microcatheter with the stent retriever (Solitaire) in it was navigated through the aspiration catheter and the deployed stented funnel over the wire until reaching and crossing the clot. The stent retriever was deployed to capture the clot while continuous aspiration was applied via ANCD, the stent retriever was dragged until the whole clot was safely placed inside the stented funnel and both devices were finally retrieved as a whole. In specific procedures aspiration was not applied.

2.5. Evaluation Methodology (1) Assessment of the Efficacy:

REVASCULARIZATION: Flow was evaluated following the procedure time points after all procedure execution. TICI 2b and 3 are considered successful revascularization (1). TICI 0, 1, and 2a are considered unsuccessful revascularization (0). Time points:
  Pre-clot placement (for baseline of model vasculature)
  Pre-treatment (baseline of ischemia, clinical starting point)
  Post-thrombectomy pass 1 ("first pass revascularization")
  Post-thrombectomy pass 2 (if appropriate)
  Post-thrombectomy pass 3 (if appropriate)

The main endpoints considered in the efficacy assessment were:
  Rate of revascularization after first pass (TICI 2b-3)
  Rate of revascularization after 3 passes (TICI 2b-3)

EMBOLIC EVENTS (ENT/EDT). Flow was evaluated following the procedure time points after all procedure execution. Distal Territory (EDT) and Emboli New Territory (ENT) are assessed. EDT score of 0 and ENT score of 0 is indicative of no embolic events. EDT score of 1 and ENT score of 1 is indicative of an embolic event. Time points:
  Pre-clot placement (for baseline of model vasculature)
  Pre-treatment (baseline of ischemia, clinical starting point)
  Post-thrombectomy pass 1 ("first pass revascularization")
  Post-thrombectomy pass 2 (if appropriate)

Post-thrombectomy pass 3 (if appropriate)
The endpoints considered in the efficacy assessment were:
EDT and ENT after first pass (TICI 2b-3)
EDT and ENT after 3 passes (TICI 2b-3)
(2) Assessment of Navigability:
Navigability was assessed after the first attempt. The following endpoints were used to assess navigability:
Navigation time [s]: the time required to reach the target vessel
Navigability/flexibility: ratio between the navigation time and the score "Pushability of the device to the target vessel. Proximal control of the device"

2.6. Experimental Design

Table 6 shows the experiments that were carried out for each group and each condition for different assessments. The maximum number of thrombectomy attempts (passes) were limited to 3.

TABLE 6

Experimental design

EFFICACY OF MARKET DEVICES ENDPOINTS

| | | | | |
|---|---|---|---|---|
| revascularization $1^{st}$ pass | revascularization $3^{rd}$ pass | Distal embolization (EDT) | | New territory embolization (EDT) |
| DEVICES | SAMPLE SIZE | VASCULAR MODEL | CLOT type | location |
| Solitaire + BGC | 10 | Jacobs | Soft red | MCA-M1 |
| | 10 | Jacobs | Fibrin rich | MCA-M1 |
| | 5 | UMASS moderate | Soft red | MCA-M1 |
| | 5 | UMASS moderate | Fibrin rich | MCA-M1 |
| | 5 | UMASS severe | Soft red | MCA-M1 |
| | 5 | UMASS severe | Fibrin rich | MCA-M1 |
| Solitaire + DAC | 5 | Jacobs | Soft red | MCA-M1 |
| | 5 | Jacobs | Fibrin rich | MCA-M1 |
| | 5 | UMASS moderate | Soft red | MCA-M1 |
| | 5 | UMASS moderate | Fibrin rich | MCA-M1 |
| | 5 | UMASS severe | Soft red | MCA-M1 |
| | 5 | UMASS severe | Fibrin rich | MCA-M1 |

EFFICACY OF ANCD COMBINED WITH STENT RETRIEVERS ENDPOINTS

| | | | | |
|---|---|---|---|---|
| revascularization $1^{st}$ pass | revascularization $3^{rd}$ pass | Distal embolization (EDT) | | New territory embolization (EDT) |
| DEVICES | SAMPLE SIZE | VASCULAR MODEL | CLOT type | location |
| ANCD + Solitaire | 7 | Jacobs | Soft red | MCA-M1 |
| | 7 | Jacobs | Fibrin rich | MCA-M1 |
| | 5 | UMASS moderate | Soft red | MCA-M1 |
| | 5 | UMASS moderate | Fibrin rich | MCA-M1 |

| DEVICES | ASPIRATION | SAMPLE SIZE | VASCULAR MODEL | CLOT type | location |
|---|---|---|---|---|---|
| ANCD + stent retriever | YES | 17 | Jacobs | Soft red | MCA-M1 |
| | | 16 | Jacobs | Fibrin rich | MCA-M1 |
| | | 5 | UMASS moderate | Soft red | MCA-M1 |
| | | 5 | UMASS moderate | Fibrin rich | MCA-M1 |

2.7. Data Analysis

Revascularization and embolization values were expressed as percentage; the mean per group was calculated.

Performance scores were qualitatively analyzed. Mean and SD per group were also calculated.

Integrity data was assessed qualitatively.

Statistical analyses of revascularization, embolization and navigability values were conducted with Excel. T-test was applied to compare means of two groups, a value of p≤0.05 was considered statistically significant.

3. Results (Expressed in %)

TABLE 7

(intrac = intracerebral):

| | Cerebrovascular models | | | | ANCD + Solitaire | | | BGC + Solitaire | | | DAC + Solitaire | | |
|---|---|---|---|---|---|---|---|---|---|---|---|---|---|
| Model | tortuosity | Index (TI) | Global TI | Clot type | n | 1st pass | 3rd pass | n | 1st pass | 3rd pass | n | 1st pass | 3rd pass |
| Jacobs | access | 2.33 | 7.08 | soft red | 10 | 100 | 100 | 10 | 100 | 100 | 10 | 80 | 90 |
| Tortuous access | intrac | 4.75 | | fibrin rich | 15 | 87 | 100 | 14 | 29 | 29 | 13 | 77 | 85 |
| UMASS | access | 0.05 | 5.88 | soft red | 10 | 100 | 100 | 10 | 80 | 80 | 10 | 90 | 100 |
| Moderate tortuosity | intrac | 5.83 | | fibrin rich | 15 | 93 | 100 | 15 | 67 | 93 | 16 | 75 | 88 |
| UMASS | access | 0.17 | 7.23 | soft red | 5 | 100 | 100 | 5 | 100 | 100 | 5 | 100 | 100 |
| Severe Tortousity | intrac | 7.07 | | fibrin rich | 5 | 100 | 100 | 5 | 60 | 80 | 6 | 100 | 100 |

Figure 25:
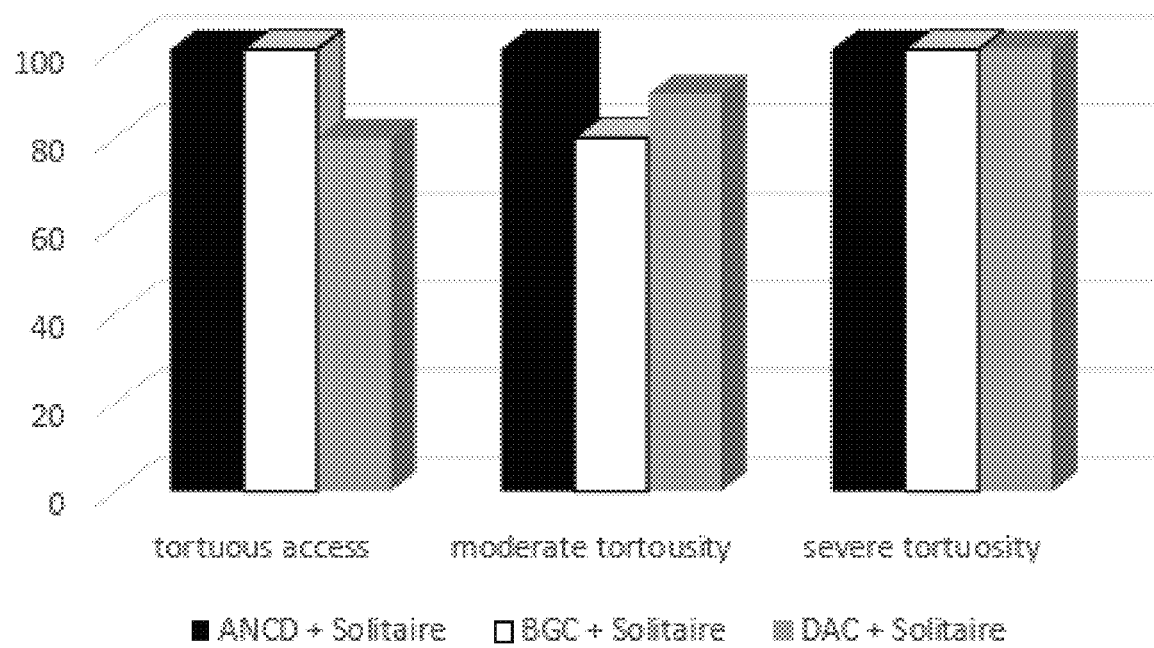
FIG. 25 shows the rate of revascularization after a single pass in different models using soft red clots.
Figure 26:
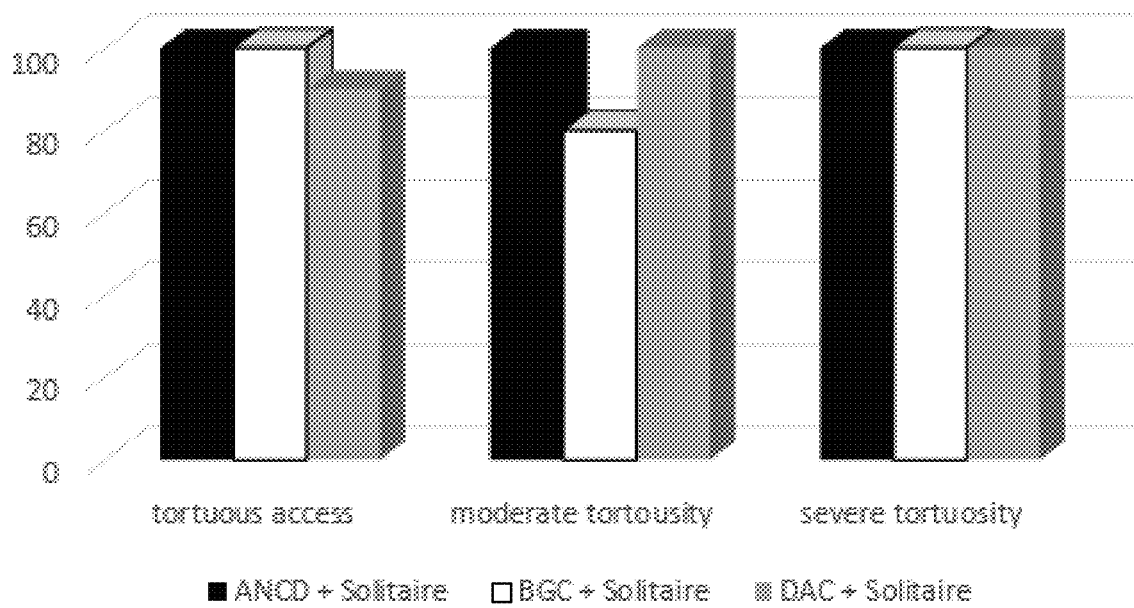
FIG. 26 shows the rate of revascularization after the third pass in different models using soft red clots.

With soft red clots the results of combining ANCD with Solitaire were better or equal than combining Solitaire with a Balloon Guiding Catheter (BGC) or a Distal Access Catheter (DAC) (FIG. 25). Similar results were observed at the first pass and at the third pass in all three models (FIG. 26).

Figure 27:
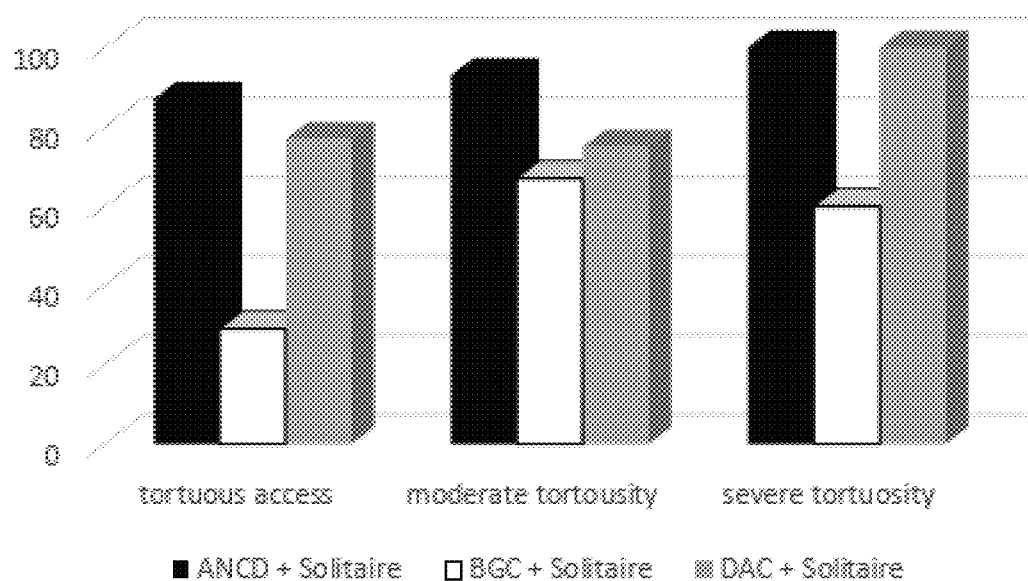
FIG. 27 shows the rate of revascularization after a single pass in different models using fibrin rich clots.
Figure 28:
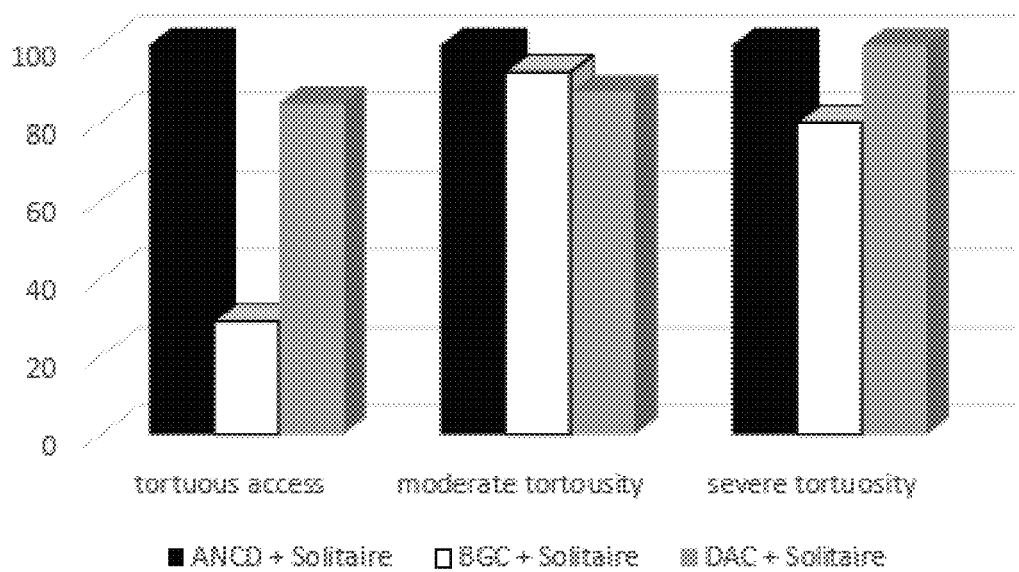
FIG. 28 shows the rate of revascularization after the third pass in different models using fibrin rich clots.

With fibrin rich clots the results of combining ANCD with Solitaire were always better than combining Solitaire with a Balloon Guiding Catheter (BGC) or a Distal Access Catheter (DAC) (FIG. 27). Similar results were observed at the first pass and at the third pass in all three models (FIG. 28).

With the other stent retrievers similar results were observed (data not shown).

4. Conclusions

The ANCD system in combination with a stent retriever showed significantly better recanalization rates in a smaller number of passes as compared to other commonly used device combinations, such as BGC or DAC in combination with a stent retriever, especially with fibrin-rich clots.

Extrapolating these results to clinical practice, it would be better to treat acute ischemic stroke on large vessel occlusion and clinical mismatch directly with ANCD combined with a stent retriever. This combination would avoid the need to use a rescue therapy.

Example 2

1. Background. This study examines the safety and efficacy of the ANCD thrombectomy system described herein in connection with FIGS. 1-5 in combination with a stent retriever in vivo.

2. Methods. In patients presenting with apparent cerebral blood clots, a 6F guide catheter (NeuronMax®, Penumbra) was placed at the level of the internal carotid artery, in a triaxial setting, and a microcatheter (e.g., Phenom 21®, Medtronic) was advanced over a microguidewire to the clot. The ANCD catheter, in its retracted position, was then positioned as close as possible to the proximal aspect of the clot (terminal internal carotid artery or middle cerebral artery) and the funnel was deployed in order to locally restrict flow. Site of deployment (i.e., below vs above carotid siphon) was recorded. The microcatheter was then advanced through the clot, and a stent retriever (SR) (Solitaire® family, Medtronic) deployed as in usual practice. At this point, the microcatheter was completely withdrawn to increase the aspiration lumen and manual aspiration (60 cc VacLok® syringe) was applied through the ANCD funnel catheter. The SR was then, slowly pulled into the funnel while applying aspiration. When the distal ends of SR and ANCD funnel catheter are aligned, assuming that the clot was mobilized and copped into the funnel, both the ANCD and the SR were simultaneously pulled out.

3. Outcomes measures. Primary efficacy outcome was defined as the ability of the ANCD device to facilitate SR deployment and, in conjunction with the SR, achieve successful reperfusion (mTICI≥2b) in the target vessel with ≤3 passes without the use of rescue therapy (intention to treat population). Rescue therapy with alternative commercially available devices was allowed after at least one attempt with the ANCD device. In cases in which rescue therapy was used before TICI2b was achieved, primary outcome was considered as not achieved. Secondary efficacy outcomes were: the ability of the ANCD catheter to reach the occlusion allowing navigation and deployment of the SR, procedural times, neurological status at day 5 or discharge and mRS at day 90. The local interventionalist and an independent central core lab assessed the rate of recanalization according to the eTICI scale, including first pass complete recanalization (mTICI 2c-3) and rate of successful recanalization (TICI 2b-3) after each pass and at the end of procedure including rescue therapy. Sudden recanalization was considered when mTICI increased from 0-1 to 2b-3 in a single pass. Only central corelab readings are presented as main results. An independent Clinical Research Organization was responsible for the monitoring of the clinical data.

Safety was defined as the occurrence of any serious adverse device effects up to 90-days post-procedure, including: symptomatic intracranial hemorrhage (sICH), neurological worsening defined as NUBS increasing ≥4 points (24 hours and 5 days or discharge), rate of embolization to distal or new territories, rate of procedural complications (arterial perforation, dissection, vasospasm in target vessel, and procedure related mortality. All reported adverse events were reviewed by an independent data safety monitoring board who adjudicated their potential relationship with the ANCD device.

4. Results 4.1 Baseline and radiological characteristics. The mean age of the patients in the study (n=35) was 74.6 years (standard deviation—SD—8.3), 54.3% (n=19) of them were women. Median admission NIHSS score was 12 (interquartile range—IQR—9-18), left hemisphere was affected in 21 (60%) patients and median ASPECTS score on initial CT was 9 (IQR 9-10). Sites of primary occlusion were: 5 (14.3%) terminal internal carotid artery (ICA), 15 (42.9%) M1 middle cerebral artery (MCA) and 15 (42.9%) M2-MCA. Other baseline characteristics are shown in Table 8.

TABLE 8

| Demographic | |
|---|---|
| Age (mean +/− SD; years) | 74.6 +/− 8.3 |
| Gender (female) | 19 (54.3%) |
| prestroke mRS (median, IQR) | 1 (0.5-1) |
| Current/previous Smoker | 7 (20%) |
| Hypertension | 28 (80%) |
| Diabetes mellitus | 12 (34.3%) |
| Dyslipidemia | 20 (57%) |
| Atrial fibrillation | 5 (14.3%) |
| Clinical and radiological | |
| NIHSS score (median, IQR) | 12 (9-18) |
| ASPECTS (median, IQR) | 9 (9-10) |
| Side of occlusion (left) | 21 (60%) |
| Occlusion site: ICA | 5 (14.3%) |
| M1-MCA | 15 (42.9%) |
| M2-MCA | 15 (42.9%) |
| Treatment | |
| Intravenous thrombolysis | 8 (22.9%) |
| Onset to groin time (median, IQR; minutes) | 240 (149-345) |
| Door to groin time (median, IQR; minutes) | 51 (34-87) |
| Procedural time (groin to procedure end time/ all sheets removed) (median, IQR; minutes) | 41 (25-57) |
| Clinical outcome | |
| NIHSS at 24 hours (median, IQR) | 5 (1-16) |
| NIHSS at 5 days (median, IQR) | 1 (1-6) |
| mRS at 90 days (median, IQR) | 1 (1-3) |
| Symptomatic hemorrhagic transformation | 2 (5.7%) |

4.2 Procedural data. Of the 35 consecutive cases (intention to treat population), ANCD could be successfully deployed in 97.1% of patients (n=34;). The ANCD funnel was deployed below the carotid siphon in 74.2% (n=26) and above the carotid siphon in 22.9% (n=8). In the remaining case, excessive vascular tortuosity led to difficult navigation and instability precluding deployment and first recanalization attempt with the ANCD device. The median procedural time was 41 (IQR 25-57) minutes.

4.3 Intention to treat analysis. Primary endpoint defined as successful reperfusion (mTICI 2b-3) within 3 passes without rescue therapy, was achieved in 91.4% (n=32) of patients with a rate of complete reperfusion (mTICI 2c-3) of 65.7%. Rate of first pass complete recanalization (mTICI≥2c) was 42.9% and rate of sudden recanalization was 82.9%. Median number of ANCD passes was 1 (IQR: 1-2). Surprisingly, the data show that deployment of the funnel below the carotid siphon provided rates of successful and complete recanalization of a cerebral artery of 96.2% and 76.9%, respectively, which is a clinical efficacy as good as, or better than, the rates of successful and complete recanalization when the funnel is deployed above the siphon (87.5% and 37.5%, respectively).

In 17.1% (n=6) patients rescue treatment was used; median number of rescue therapy passes was 2 (1-7) leading to a rate of final successful reperfusion of 94.3% (n=33) patients.

The detailed results of the endpoints values (percentage of patients) for the efficacy and safety performance comparing the deployment site (below the siphon vs above the siphon) are shown in Table 9 (percentage of all patients) and Table 10 (percentage of patients with thrombus located in M1 segment), respectively.

TABLE 9

| | Below Siphon | Above Siphon | p-value |
|---|---|---|---|
| Complete revascularization (1st pass) | 50% | 25% | |
| Complete revascularization (including 1st and 3rd passes) | 77% | 38% | p = 0.08 |
| Successful reperfusion (including 1st) | 62% | 50% | |
| Successful reperfusion (including 1st and 3rd passes) | 96% | 88% | p = 0.42 |
| Sudden recanalization | 85% | 75% | — |
| mRS <= 2 at 90 days | 62% | 50% | — |
| Mortality at 90 days | 19% | 25% | — |
| Rescue therapy | 8% | 38% | — |
| Number of passes | 1.77 | 3.13 | — |
| Average procedure time | 50 minutes | 60 minutes | — |
| Thrombus in M1 segment | 31% | 88% | — |

TABLE 10

| | Below Siphon | Above Siphon |
|---|---|---|
| Complete revascularization (1st pass) | 25% | 14% |
| Complete revascularization (including 1st and 3rd passes) | 63% | 29% |
| Successful reperfusion (1st pass) | 63% | 43% |
| Successful reperfusion (including 1st and 3rd passes) | 100% | 86% |
| Sudden recanalization | 75% | 71% |
| mRS <= 2 at 90 days | 63% | 57% |
| Mortality at 90 days | 38% | 29% |
| Rescue therapy | 13% | 43% |
| Number of passes | 2.12 | 3.4 |
| Average procedure time | 46 minutes | 66 minutes |

4.4 Safety and clinical outcomes. Rate of symptomatic intracranial hemorrhage was 5.7% (n=2). One patient, in which stroke etiology was presumed to be intracranial atherosclerotic disease presented an intracranial vessel perforation while receiving rescue angioplasty treatment. In two other patients a periprocedural dissection of the extracranial ICA was observed (one required stenting). One patient presented an embolization into a new vascular territory. Data safety monitoring board reviewed all reported adverse events and concluded that there are no safety concerns related with the use of the ANCD device.

At 5 days or discharge median NIHSS was 1 (IQR 1-6). At 3 months, favorable functional outcome, defined as mRS 0-2, was achieved in 60.0% patients (n=21) and mortality rate was 20% (n=7).

5. Conclusions

The ANCD device was originally conceived to be deployed intracranially, very proximal to the clot. However, as recruitment of patients progressed, we observed that funnel deployment at a lower level (i.e., proximal to the carotid siphon) did not seem to reduce the efficacy of clot retrieval and recanalization. We therefore conclude that, unexpectedly, the ANCD thrombectomy system described in connection with FIGS. 1-5 herein may be used to retrieve a cerebral clot by deploying the funnel proximal to the distal end of the carotid siphon, or proximal to the proximal end of the carotid siphon.

Example 3

1. Background

Example 1 addressed the superiority of the ANCD thrombectomy system described herein in connection with FIGS. 1-5 in combination with a stent retriever in terms of in vitro revascularization to a Balloon Guiding Catheter (BGC) or a Distal Access Catheter (DAC) in combination with stent retriever, especially with fibrin rich clots. Example 2 addressed the safety and efficacy of the ANCD thrombectomy system described herein in connection with FIGS. 1-5 in combination with a stent retriever in vivo. This Example 3 identifies the physical properties of the ANCD system and its use with a stent retriever that are responsible for the superior results discussed in Example 1-2.

2. Methods 2.1 Experimental method. To empirically examine the performance of the ANCD design, the ANCD has been tested against commercially available catheters (Table 11). All experiments were performed without a stent retriever (SR) and repeated including a SR (Solitaire2® 4×40 and 6×20 mm; Medtronic, Minneapolis, MN), to characterize its potential impact on aspiration flow and suction force.

TABLE 11

| Outer Diameter | Catheter | Company | Distal ID (in) | Proximal ID (in) | Distal Area (in$^2$) | Length of the tube (cm) |
|---|---|---|---|---|---|---|
| 6F | ACE68 | Penumbra Alameda, CA | 0.068 | 0.068 | 0.0036 | 132 |
| 6F | NAVIEN 072 | Medtronic Minneapolis, MN | 0.072 | 0.072 | 0.0041 | 125 |
| 6F | 4Max | Penumbra Alameda, CA | 0.041 | 0.064 | 0.0013 | 139 |
| 6F** | ANCD | Anaconda Biomed, S.L Barcelona, Spain | 0.196 | 0.047 | 0.03 | 138 |
| 8F | NeuronMax | Penumbra Alameda, CA | 0.088 | 0.088 | 0.0061 | 80 |
| 8F | CELLO | Medtronic Minneapolis, MN | 0.075 | 0.075 | 0.0044 | 95 |
| 8F | Flowgate2 | Stryker Kalamazoo, MI | 0.083 | 0.083 | 0.005 | 95 |

Figure 29:
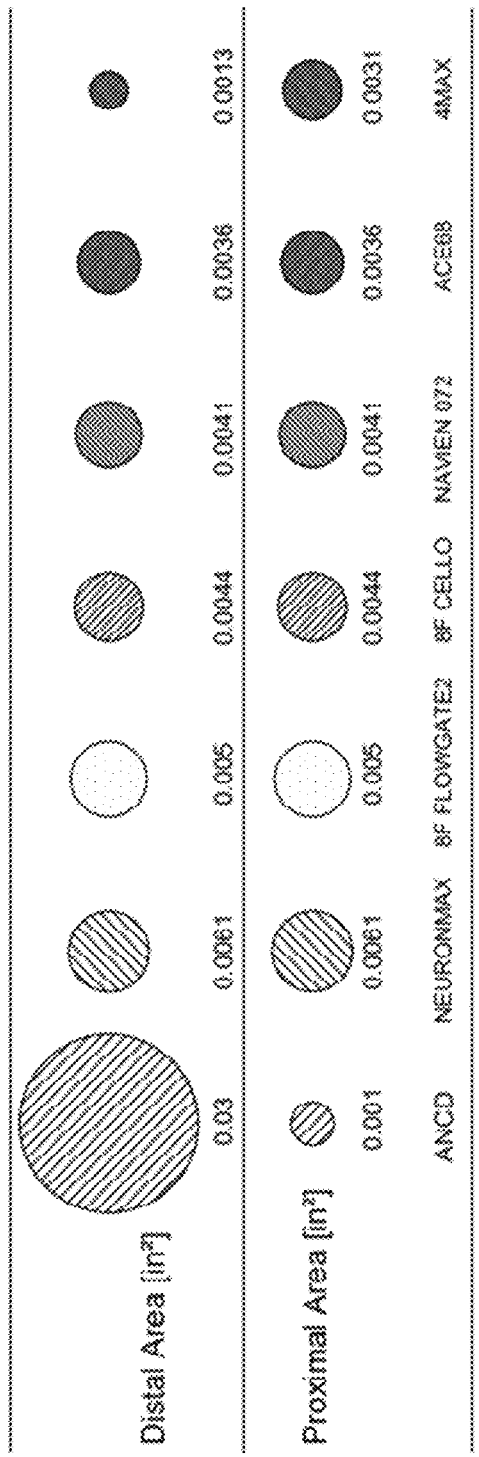
FIG. 29 shows proximal and distal cross-sectional areas of catheters employed in a suction test.

The proximal and distal cross-sectional areas of the different catheters are represented in FIG. 29.

2.2 Suction force evaluation. In this experiment, the thrombus shape and stiffness were simulated using a polyurethane tool attached to a tensile tester. For the evaluation of the suction force of the catheters, the experimental model shown in FIGS. 30A-F has been used:

The INSTRON-EQ152® (Instron, Norwood, MA) tensile tester with a 10N load cell was used. A specially designed clot analog was connected to the load cell. The clot analog occluded the inner tip of the catheters selected for this study. Once the clot analog in place, a negative pressure of 500 mmHg was applied using a VacMaxi® pump (APEX MEDICAL Corp., New Taipei City, Taiwan) intended for suction. Then the clot analog was pulled away from the catheter at a constant speed of 50 mm/min, and the force necessary to separate the clot from the tip of the catheter was evaluated, as illustrated in FIGS. 30A-F. A minimum sample size of three was used and the mean value of all measurements was used for comparisons.

Figure 31:
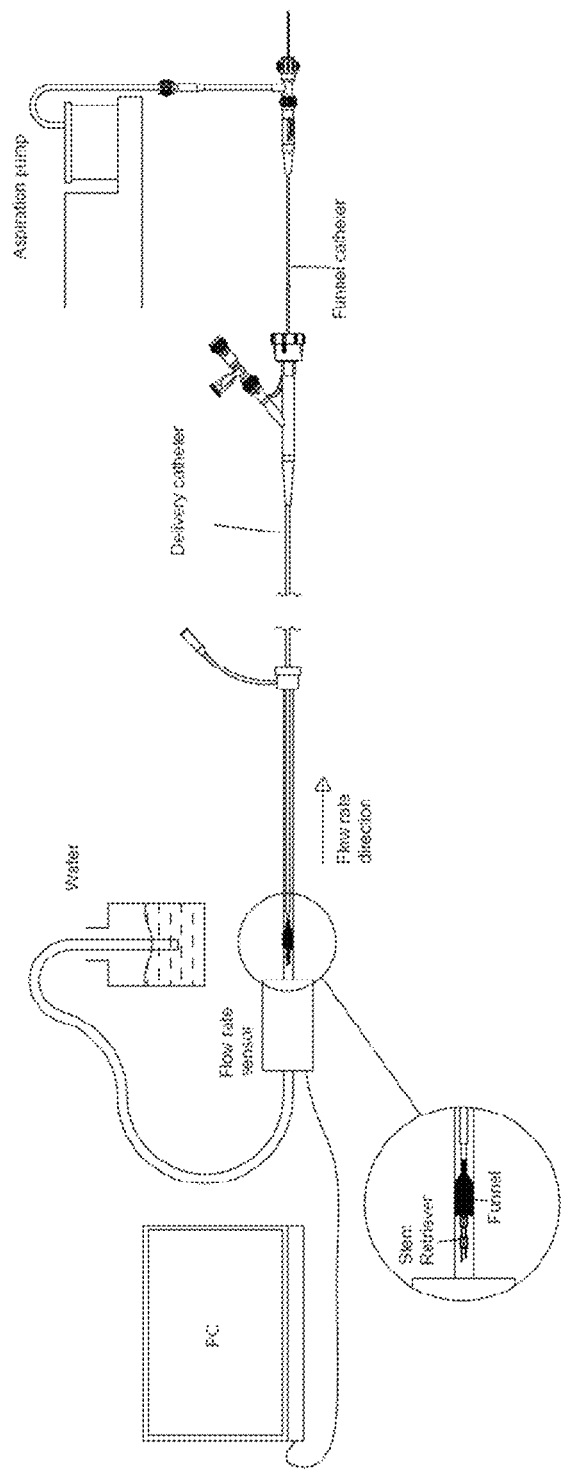
FIG. 31 shows an experimental set-up to test aspiration flow.

2.3 Aspiration flow evaluation. An ultrasonic flow sensor (Sonotec® CO.55/0.35 V2.0, SONOTEC GmbH, Saale, Germany) was connected as shown in FIG. 31. Once the circuit was assembled, the tested catheter was inserted to a position close to the sensor. The catheter was connected to the vacuum pump. Then, a negative pressure of 500 mmHg was applied using a VacMaxi pump (APEX MEDICAL Corp., New Taipei City, Taiwan). The aspiration flow rate was measured in a stationary state for 30 seconds for each sample. A minimum sample size of three was used and the mean value of all measurements was used for comparisons.

2.4 Balloon lifting experiment. Rubber balloons were filled with 1, 10, 13, 15, and 17 g of water. A negative pressure of 130 mmHg was applied through the tested catheter. The tip of the catheter was brought into contact with the balloon apex. The balloon was lifted vertically. A failure was registered if the catheter was unable to hold the balloon in the air for at least 3 seconds. Four consecutive attempts were permitted. The maximum weight lifted was registered for each catheter.

2.5 Statistical analysis. Statistical analysis and comparisons were made using the Minitab® statistical package (Minitab LLC, State College, Pennsylvania). Continuous variables were tested for normality using the Shapiro-Wilk test; and presented as mean and standard deviation (SD) or median and interquartile range if not normally distributed. Univariate comparisons of means were performed by Student's t-test, a probability value of $p<0.05$ was considered significant for all the results.

3. Results

Aspiration flow increased with the inner diameter of the device: ANCD 1.84±0.05 mL/s, ACE68. 3.75±0.05 mL/s, 8F Flowgate2 5.9±0.3 mL/s ($p<0.001$). After introducing the SR the flow was reduced by an average of 0.57±0.13 mL/s. The suction force was proportional to the inner surface of the distal tip of the device in contact with the clot: ANCD 1.7±0.4N, ACE68 0.26±0.02N, 8F Flowgate2 0.41±0.06N ($p<0.001$). After introducing the SR, the variation of suction force was not relevant except for ANCD that increased to 2.5N±0.4N.

Figure 32A:
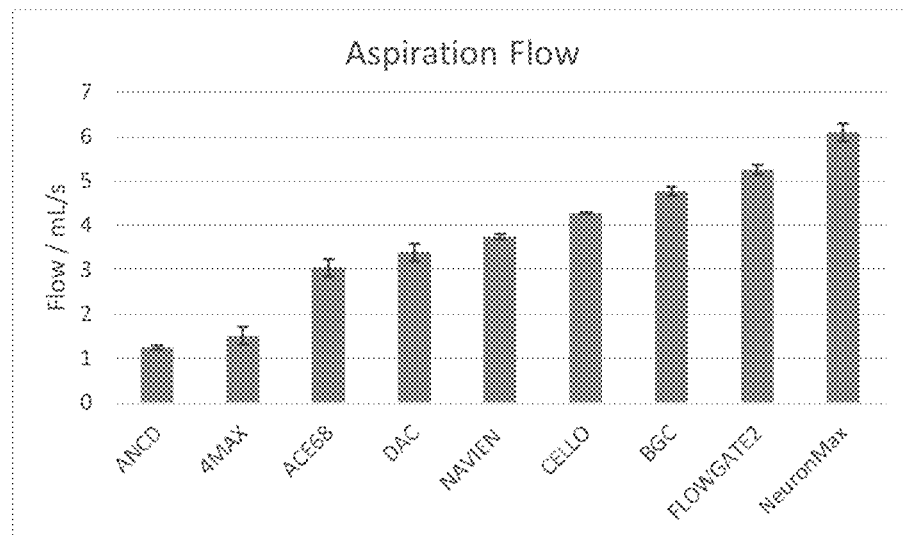
FIGS. 32A-B show aspiration flow and suction force data for various catheters.
Figure 32B:
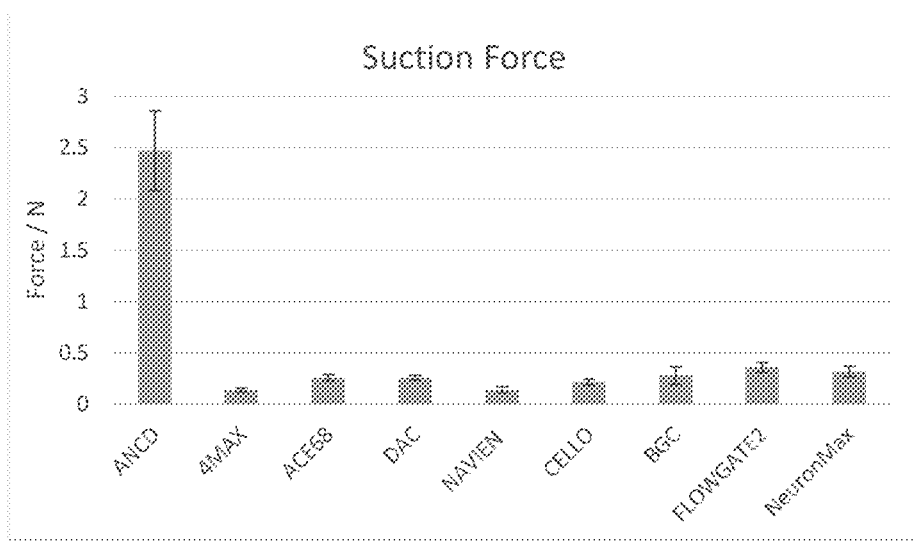

All tests were performed with consistent experimental conditions to limit confounding variables. The results obtained in the exploratory testing are presented in Table 12 and represented graphically in FIGS. 32A-B (Aspiration Flow and Suction Force (with SR)). The data show that ANCD has the lowest aspiration flow rate but the highest suction force. DAC refers to the combination of ACE68 and NAVIEN 072 while BGC is the combination of 8F CELLO and 8F Flowgate2.

TABLE 12

| SR | catheter | Proximal ID (in) | Flow/ mL·s$^{-1}$ | Std. Deviation/ mL·s$^{-1}$ | Force/ N | Std. Deviation/ N |
|---|---|---|---|---|---|---|
| no | ANCD | 0.047 | 1.84 | 0.05 | 1.73 | 0.37 |
| yes | ANCD | 0.047 | 1.24 | 0.05 | 2.47 | 0.39 |
| no | 8F CELLO | 0.075 | 4.94 | 0.07 | 0.22 | 0.03 |
| yes | 8F CELLO | 0.075 | 4.28 | 0.02 | 0.22 | 0.03 |
| no | 8F FLOWGATE2 | 0.083 | 5.9 | 0.3 | 0.41 | 0.06 |
| yes | 8F FLOWGATE2 | 0.083 | 5.26 | 0.1 | 0.36 | 0.05 |
| no | ACE68 | 0.068 | 3.75 | 0.05 | 0.26 | 0.02 |
| yes | ACE68 | 0.068 | 3.05 | 0.2 | 0.26 | 0.03 |
| no | NAVIEN 072 | 0.072 | 4.3 | 0.04 | 0.19 | 0.01 |
| yes | NAVIEN 072 | 0.072 | 3.74 | 0.06 | 0.14 | 0.03 |

TABLE 12-continued

| SR | catheter | Proximal ID (in) | Flow/ mL·s$^{-1}$ | Std. Deviation/ mL·s$^{-1}$ | Force/ N | Std. Deviation/ N |
|---|---|---|---|---|---|---|
| no | NeuronMax | 0.088 | 6.4 | 0.02 | 0.35 | 0.02 |
| yes | NeuronMax | 0.088 | 6.1 | 0.2 | 0.32 | 0.05 |
| no | 4MAX | 0.064 | 2.06 | 0.02 | 0.1 | 0.01 |
| yes | 4MAX | 0.064 | 1.51 | 0.2 | 0.14 | 0.02 |

The achieved aspiration flow rates followed Hagen-Poiseuille Law ($R^2$=0.9883). The suction forces where directly proportional to the inner surface of the catheters tips ($R^2$>0.99) and where similar for all tested catheters (values between 0.10 and 0.41 N without SR and 0.22-0.36N with SR) except for ANCD in which the force was significantly augmented by the association with the SR (1.7N±0.4N ($p<0.001$) without SR and 2.5N±0.4N ($p<0.001$) with SR).

The balloon lifting experiment was performed with ACE68 and with ANCD. ACE68 lifted 0 g while ANCD lifted 15 g.

4. Conclusions

Figure 33:
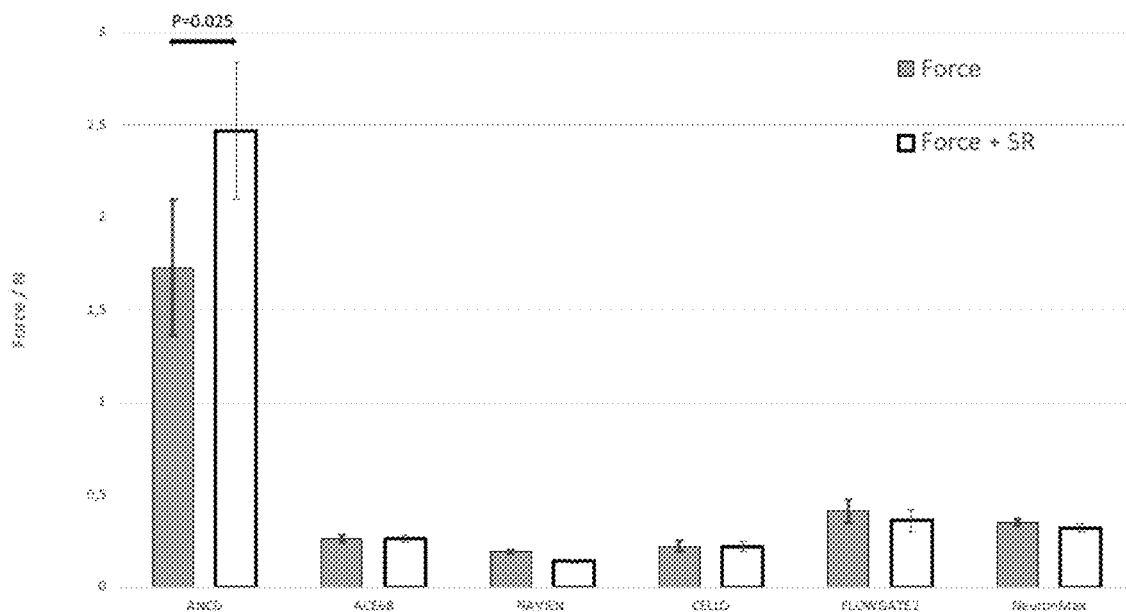
FIG. 33 shows suction force with a stent retriever and suction force without a stent retriever for various catheters.

Our study shows that ANCD despite a lower aspiration flow induces the highest suction force of all tested devices. The dragging force generated when aspiration is applied is highly determined by the contact area between the catheter and the clot and therefore the distal area of the ANCD explains the superior suction force registered (FIG. 33, which shows suction force with SR vs. suction force without SR). When comparing the suction force of ANCD with (2.5±0.4N) and without (1.7±0.4N) a SR, we observed a synergistic effect leading to a 30% force increase that was not seen with other devices (see FIG. 33). This synergy could be explained by the extra radial force of the SR that prevents the funnel from collapsing at high vacuum. This high suction force may be responsible for the observed improved efficacy profile of ANCD in terms of complete recanalization when attempting to retrieve hard non-deformable clots. A high catheter to vessel diameter ratio correlates with recanalization. The design of ANCD allowing distal tip expansion up to the size of the target vessel ensures the highest catheter to vessel ratio in every case.

The study breaks the paradigm that a higher flow is needed to better extract the clot. Aspiration flow during EVT is created to mobilize the occluding clot into the catheter and eventually away from the cerebral vessels. If flow is maintained the procedure may be effective dragging out the whole clot or its fragments. However, if for any reason the aspiration flow is stopped (e.g., hard clot occluding the aspiration catheter) the success of the procedure relies on the suction force generated at the distal end of the catheter. ANCD not only induces the highest suction force but also reduces the probability of fragmentation at the distal and of the clot by protecting its integrity inside the funnel. Our study design represents a clinically relevant approach to what happens in a scenario in which a hard thrombus (rigid material) is completely occluding the tip of the catheter. The larger and more flexible tip of the ANCD funnel creates an efficient suction trap that also generates local flow arrest. The combination of these features minimizes undesired events such as clot separation, fragmentation, roll-out or shaving during aspiration and extraction.

Figure 34:
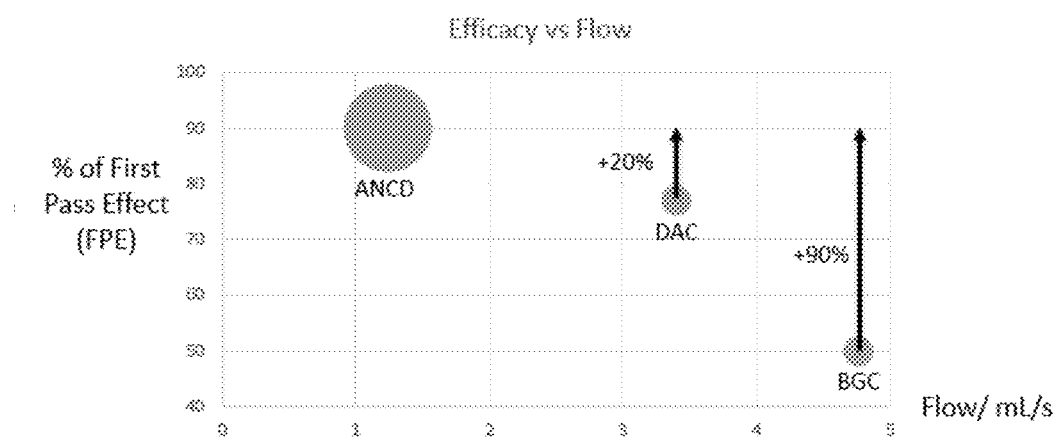
FIG. 34 is a chart comparing clot capture efficacy of various catheters with suction flow rate.

The results for ACE68® and Navien® 072 were pooled together in the category Distal Access Catheters (DAC) while the results of 8 French Cello® and 8 French Flowgate2® where pooled in the Balloon Guiding Catheter (BGC) category. Table 13 and FIG. 34 compare the results of the present study to the results obtained by Sanchez et al. with hard fibrin rich clots in phantom models of different tortuosities: higher aspiration flow rates do not correlate with higher clot capture efficacy, suggesting that in hard clot models, suction force is more important than aspiration flow in terms of efficacy. In pre-clinical observations, the observed increase in suction force with the ANCD did not represent an additional procedural risk in terms of endothelial damage.

TABLE 13

| | In-vitro FPE Fibrin Rich Clot | OD | Flow | Force |
|---|---|---|---|---|
| ANCD + SR | 90% | 6F | 1.2 mL/s | 2.5 N |
| DAC + SR | 77% | 6F | 3.3 mL/s | 0.3 N |
| BGC + SR | 50% | 8F | 4.8 mL/s | 0.3 N |

Despite showing a lower in-vitro aspiration flow, the ANCD design, with its funnel that expands to the walls of the blood vessel, demonstrates a substantial increase in clot suction force compared to other thrombectomy devices. In addition, use of a stent retriever with the ANCD funnel provides a synergistic increase of the suction force applied by the funnel.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of extracting a thrombus from a thrombus site in a cerebral artery of a patient, the method comprising:
    advancing a first catheter through vasculature of the patient into an internal carotid artery of the patient;
    advancing a clot-mobilizer distally through the first catheter toward the thrombus and beyond the carotid siphon;
    deploying the clot-mobilizer;
    engaging thrombus material from the thrombus with the clot-mobilizer;
    advancing a funnel catheter within the first catheter, a funnel being disposed on a distal end of the funnel catheter;
    moving the funnel catheter and the first catheter with respect to each other to place the funnel outside of the first catheter;
    expanding the funnel into contact with an inner wall of the internal carotid artery at or proximal to the proximal end of the carotid siphon, thereby reducing blood flow past the funnel;
    applying suction through the funnel catheter to the funnel to aspirate thrombus material;
    moving the clot-mobilizer and thrombus material proximally at least partially into the funnel; and
    moving the funnel, the clot-mobilizer and the thrombus material proximally within the vasculature.

2. The method of claim 1, wherein the step of deploying the clot-mobilizer comprises expanding the clot-mobilizer into contact with an arterial wall.

3. The method of claim 1, wherein the first catheter is a guide catheter or a sheath.

4. The method of claim 1, wherein the funnel adapts its shape and length to the vasculature as it moves proximally within the vasculature by lengthening as it narrows to retain the thrombus material at least partially within the funnel.

5. The method of claim 1, wherein the clot-mobilizer is carried by a microcatheter.

6. The method of claim 1, wherein advancing the clot-mobilizer comprises advancing a microcatheter carrying a clot-mobilizer through a lumen of the funnel toward the thrombus site and into the thrombus.

7. The method of claim 1, wherein deploying the clot-mobilizer comprises retracting the microcatheter to deploy the clot-mobilizer.

* * * * *